(12) United States Patent
Furner et al.

(10) Patent No.: US 7,954,667 B2
(45) Date of Patent: Jun. 7, 2011

(54) COMPACT SPRAY DEVICE

(75) Inventors: Paul E. Furner, Racine, WI (US); Thomas P. Gasper, Germantown, WI (US); Chris A. Kubicek, East Troy, WI (US); Leon M. Lemon, Mendon, UT (US); Brent D. Madsen, Providence, UT (US); Nathan R. Westphal, Union Grove, WI (US); Kenneth W. Michaels, Spring Grove, IL (US); Cory J. Nelson, Racine, WI (US); M. Scott Carpenter, Racine, WI (US); Michael E. Short, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 12 days.

(21) Appl. No.: 12/796,440

(22) Filed: Jun. 8, 2010

(65) Prior Publication Data

US 2010/0243673 A1 Sep. 30, 2010

Related U.S. Application Data

(62) Division of application No. 11/247,793, filed on Oct. 11, 2005, now Pat. No. 7,837,065.

(60) Provisional application No. 60/617,950, filed on Oct. 12, 2004.

(51) Int. Cl.
*B67D 1/00* (2006.01)
*G04C 1/12* (2006.01)
*A01G 27/00* (2006.01)

(52) U.S. Cl. .......... 222/52; 222/644; 222/646; 222/647; 222/649; 222/504; 239/70; 239/337

(58) Field of Classification Search .............. 222/64, 222/61, 62, 52, 638, 639, 642, 643, 644, 222/645, 646, 647, 648, 649, 504, 333, 402.13, 402.15; 239/69, 70, 333, 337
See application file for complete search history.

(56) References Cited

U.S. PATENT DOCUMENTS

D48,809 S 4/1916 Baldwin
(Continued)

FOREIGN PATENT DOCUMENTS

AU 4932300 11/2000
(Continued)

OTHER PUBLICATIONS

Web Page "AirWick Fresh Matic" @ http://www.gnpd.com/sinatra/gnpd&lang=uk/images/zoom&id=342358&pic_num=0&xOff . . . dated Mar. 7, 2005 (1 page).
(Continued)

*Primary Examiner* — Kevin P Shaver
*Assistant Examiner* — Stephanie E Williams

(57) ABSTRACT

A method of operating a dispensing unit includes the step of providing a power source to a dispensing unit that includes a housing having an aerosol container disposed therein and an actuator arm. Other steps include activating the dispensing unit in response to a minimum threshold of light being sensed by a light sensor and selecting a sleep period interval between spray operations. Yet another step includes moving the actuator arm after completion of a startup delay period from a pre-actuation position to a discharge position along a path substantially parallel to an axial length of the container to actuate a nozzle of the container to discharge a fluid from the container. The method also includes the step of alternating automatically between the sleep period having a duration commensurate with the selected sleep period interval and a discharge period during which the fluid is dispensed from the container.

7 Claims, 21 Drawing Sheets

U.S. PATENT DOCUMENTS

| | | | |
|---|---|---|---|
| D84,253 S | 5/1931 | McFadden | |
| D103,209 S | 2/1937 | Beiser | |
| D128,935 S | 8/1941 | Derham et al. | |
| 2,550,825 A | 5/1951 | Kolodie | |
| 2,613,108 A | 10/1952 | Krause | |
| D180,916 S | 9/1957 | Perlman | |
| 2,928,573 A | 3/1960 | Edelstein | |
| 2,971,382 A | 2/1961 | Harris | |
| 3,018,056 A | 1/1962 | Montgomery | |
| 3,127,060 A | 3/1964 | Vosbikian et al. | |
| 3,138,331 A | 6/1964 | Kutik | |
| 3,165,238 A | 1/1965 | Willey | |
| 3,185,356 A | 5/1965 | Venus, Jr. | |
| 3,187,948 A | 6/1965 | Hunt | |
| 3,187,949 A | 6/1965 | Mangel | |
| 3,199,732 A | 8/1965 | Strachan | |
| 3,228,609 A | 1/1966 | Edelstein et al. | |
| 3,240,389 A | 3/1966 | Genua | |
| 3,289,886 A | 12/1966 | Goldsholl et al. | |
| 3,305,134 A | 2/1967 | Carmichael et al. | |
| 3,326,418 A | 6/1967 | Kropp | |
| 3,368,717 A | 2/1968 | Weber | |
| 3,388,834 A | 6/1968 | Hart | |
| 3,398,864 A | 8/1968 | Kolodziej | |
| 3,419,189 A | 12/1968 | Iketani | |
| 3,472,457 A | 10/1969 | McAvoy | |
| 3,477,613 A | 11/1969 | Mangel | |
| 3,497,108 A | 2/1970 | Mason | |
| 3,498,504 A | 3/1970 | Wilkins | |
| 3,542,248 A | 11/1970 | Mangel | |
| 3,543,122 A | 11/1970 | Klebanoff et al. | |
| 3,584,766 A | 6/1971 | Hart | |
| 3,587,332 A | 6/1971 | Bell | |
| 3,589,563 A | 6/1971 | Carragan et al. | |
| 3,615,041 A | 10/1971 | Bischoff | |
| 3,627,176 A | 12/1971 | Sailors | |
| 3,643,836 A | 2/1972 | Hunt | |
| 3,658,209 A | 4/1972 | Freeman et al. | |
| 3,664,548 A | 5/1972 | Broderick | |
| 3,666,144 A | 5/1972 | Winder | |
| 3,726,437 A | 4/1973 | Siegel | |
| 3,732,509 A | 5/1973 | Florant et al. | |
| 3,739,944 A | 6/1973 | Rogerson | |
| 3,758,002 A | 9/1973 | Doyle et al. | |
| 3,779,425 A | 12/1973 | Werner | |
| 3,784,061 A | 1/1974 | Hogan | |
| 3,817,429 A | 6/1974 | Smrt | |
| 3,837,532 A | 9/1974 | Sahatjian et al. | |
| 3,841,525 A | 10/1974 | Siegel | |
| 3,865,275 A | 2/1975 | De Nunzio | |
| 3,870,274 A | 3/1975 | Broe | |
| 3,929,259 A | 12/1975 | Fegley et al. | |
| 3,952,916 A * | 4/1976 | Phillips | 222/645 |
| 3,968,905 A | 7/1976 | Pelton | |
| 3,974,941 A | 8/1976 | Mettler | |
| 3,980,205 A | 9/1976 | Smart | |
| RE29,117 E | 1/1977 | Sahajian et al. | |
| D243,017 S | 1/1977 | Fossella | |
| 4,004,550 A | 1/1977 | White et al. | |
| 4,006,844 A | 2/1977 | Corris | |
| 4,011,927 A | 3/1977 | Smith | |
| 4,063,664 A | 12/1977 | Meetze, Jr. | |
| 4,068,575 A | 1/1978 | Difley et al. | |
| 4,068,780 A | 1/1978 | Fegley | |
| 4,077,542 A | 3/1978 | Petterson | |
| 4,184,612 A | 1/1980 | Freyre | |
| 4,235,373 A | 11/1980 | Clark | |
| 4,238,055 A | 12/1980 | Staar | |
| 4,396,152 A | 8/1983 | Abplanalp | |
| 4,483,466 A | 11/1984 | Gutierrez | |
| 4,544,086 A | 10/1985 | Hill et al. | |
| 4,572,410 A | 2/1986 | Brunet | |
| 4,666,638 A | 5/1987 | Baker et al. | |
| 4,671,435 A | 6/1987 | Stout et al. | |
| 4,690,312 A | 9/1987 | Crapser et al. | |
| 4,695,435 A | 9/1987 | Spector | |
| 4,798,935 A | 1/1989 | Pezaris | |
| 4,801,093 A | 1/1989 | Brunet et al. | |
| 4,816,951 A | 3/1989 | Zago | |
| 4,830,791 A | 5/1989 | Murderlak et al. | |
| 4,877,989 A | 10/1989 | Drews et al. | |
| D309,943 S | 8/1990 | Jones et al. | |
| 4,967,935 A | 11/1990 | Celest | |
| 4,989,755 A | 2/1991 | Shiau | |
| 5,014,881 A | 5/1991 | Andris | |
| 5,014,884 A | 5/1991 | Wunsch | |
| 5,018,963 A | 5/1991 | Diedrich | |
| 5,025,516 A | 6/1991 | Wilson | |
| 5,025,962 A | 6/1991 | Renfro | |
| 5,038,972 A * | 8/1991 | Muderlak et al. | 222/25 |
| 5,055,822 A | 10/1991 | Campbell et al. | |
| D323,554 S | 1/1992 | Hoyt et al. | |
| 5,105,133 A | 4/1992 | Yang | |
| 5,134,961 A | 8/1992 | Giles et al. | |
| D329,170 S | 9/1992 | Hoffer | |
| 5,175,791 A | 12/1992 | Muderlak et al. | |
| 5,198,157 A | 3/1993 | Bechet | |
| 5,221,025 A | 6/1993 | Privas | |
| 5,230,837 A | 7/1993 | Babasade | |
| 5,243,326 A | 9/1993 | Disabato | |
| 5,249,718 A | 10/1993 | Muderlak | |
| 5,269,445 A | 12/1993 | Tobler | |
| D350,192 S | 8/1994 | Patel et al. | |
| 5,337,926 A | 8/1994 | Drobish et al. | |
| 5,337,929 A | 8/1994 | van der Heijden | |
| 5,342,584 A | 8/1994 | Fritz et al. | |
| 5,353,744 A | 10/1994 | Custer | |
| 5,358,147 A | 10/1994 | Adams et al. | |
| D352,236 S | 11/1994 | Althaus | |
| 5,383,580 A | 1/1995 | Winder | |
| RE34,847 E | 2/1995 | Muderlak et al. | |
| 5,392,768 A | 2/1995 | Johansson et al. | |
| 5,394,866 A | 3/1995 | Ritson et al. | |
| 5,397,028 A | 3/1995 | Jesadanont | |
| 5,434,386 A | 7/1995 | Glenn et al. | |
| 5,445,324 A | 8/1995 | Berry et al. | |
| 5,449,117 A | 9/1995 | Muderlak et al. | |
| 5,450,336 A | 9/1995 | Rubsamen et al. | |
| 5,487,502 A | 1/1996 | Liao | |
| 5,489,047 A | 2/1996 | Winder | |
| 5,497,764 A | 3/1996 | Ritson et al. | |
| 5,499,016 A | 3/1996 | Pantus | |
| 5,503,303 A | 4/1996 | LaWare et al. | |
| 5,520,166 A | 5/1996 | Ritson et al. | |
| 5,522,378 A | 6/1996 | Ritson et al. | |
| 5,531,344 A | 7/1996 | Winner | |
| 5,542,605 A | 8/1996 | Campau | |
| 5,591,409 A | 1/1997 | Watkins | |
| 5,622,162 A | 4/1997 | Johansson et al. | |
| D380,257 S | 6/1997 | Ganor | |
| D380,258 S | 6/1997 | Muller et al. | |
| D380,821 S | 7/1997 | Chen | |
| 5,647,388 A | 7/1997 | Butler, Jr. et al. | |
| 5,657,910 A | 8/1997 | Keyser | |
| 5,673,825 A | 10/1997 | Chen | |
| 5,676,283 A | 10/1997 | Wang | |
| D386,564 S | 11/1997 | Mycroft | |
| 5,685,456 A | 11/1997 | Goldstein | |
| 5,695,091 A | 12/1997 | Winings et al. | |
| 5,702,036 A | 12/1997 | Ferrara | |
| 5,735,918 A | 4/1998 | Barradas | |
| 5,743,251 A | 4/1998 | Howell et al. | |
| 5,743,252 A | 4/1998 | Rubsamen et al. | |
| 5,755,218 A | 5/1998 | Johansson et al. | |
| D395,494 S | 6/1998 | Becker | |
| 5,772,074 A | 6/1998 | Dial et al. | |
| 5,787,947 A | 8/1998 | Hertsgaard | |
| 5,791,524 A | 8/1998 | Demarest | |
| 5,806,697 A | 9/1998 | Harbutt et al. | |
| 5,810,265 A | 9/1998 | Cornelius et al. | |
| 5,811,766 A | 9/1998 | Fabrikant et al. | |
| 5,823,390 A | 10/1998 | Muderlak et al. | |
| 5,826,570 A | 10/1998 | Goodman et al. | |
| 5,853,129 A | 12/1998 | Spitz | |
| 5,862,844 A | 1/1999 | Perrin | |
| 5,884,808 A | 3/1999 | Muderlak et al. | |
| 5,908,140 A | 6/1999 | Muderlak | |

| | | | | | | |
|---|---|---|---|---|---|---|
| 5,922,247 | A | 7/1999 | Shoham et al. | D488,548 | S | 4/2004 | Lablaine |
| 5,924,597 | A | 7/1999 | Lynn | D488,809 | S | 4/2004 | Kamegi |
| 5,924,606 | A | 7/1999 | Huizing | 6,722,529 | B2 | 4/2004 | Ceppaluni et al. |
| 5,938,076 | A | 8/1999 | Ganzeboom | 6,739,479 | B2 | 5/2004 | Contadini et al. |
| 5,962,930 | A | 10/1999 | Cluff et al. | D491,798 | S | 6/2004 | Buthier |
| 5,964,403 | A | 10/1999 | Miller et al. | 6,769,580 | B2 | 8/2004 | Muderlak et al. |
| 6,000,658 | A | 12/1999 | McCall, Jr. | D496,719 | S | 9/2004 | Song |
| 6,006,957 | A | 12/1999 | Kunesh | 6,785,911 | B1 | 9/2004 | Percher |
| 6,026,987 | A | 2/2000 | Burnett et al. | 6,790,408 | B2 | 9/2004 | Whitby et al. |
| 6,029,659 | A | 2/2000 | O'Connor | 6,795,645 | B2 | 9/2004 | Hygema et al. |
| 6,036,108 | A | 3/2000 | Chen | 6,830,164 | B2 | 12/2004 | Michaels et al. |
| 6,039,212 | A | 3/2000 | Singh | 6,832,701 | B2 | 12/2004 | Schiller |
| D425,190 | S | 5/2000 | Morikawa | 6,837,396 | B2 | 1/2005 | Jaworski et al. |
| D426,293 | S | 6/2000 | Tounsi et al. | 6,877,636 | B2 | 4/2005 | Speckhart et al. |
| 6,092,912 | A | 7/2000 | Nelson | D508,284 | S | 8/2005 | Butler et al. |
| D432,637 | S | 10/2000 | Mertens | D508,558 | S | 8/2005 | Wolpert et al. |
| D433,113 | S | 10/2000 | Cole | 6,926,002 | B2 | 8/2005 | Scarrott et al. |
| D433,193 | S | 10/2000 | Gaw et al. | 6,926,172 | B2 | 8/2005 | Jaworski et al. |
| D434,482 | S | 11/2000 | Cole | 6,926,211 | B2 | 8/2005 | Bryan et al. |
| 6,145,712 | A | 11/2000 | Benoist | D509,892 | S | 9/2005 | McLeish |
| D435,098 | S | 12/2000 | Kemmis et al. | 6,938,796 | B2 | 9/2005 | Blacker et al. |
| 6,158,486 | A | 12/2000 | Olson et al. | D510,423 | S | 10/2005 | Caserta et al. |
| D436,398 | S | 1/2001 | Steiner | D511,452 | S | 11/2005 | Dibnah et al. |
| 6,182,904 | B1 | 2/2001 | Ulczynski et al. | D512,769 | S | 12/2005 | Wefler |
| D439,320 | S | 3/2001 | Lee | 6,971,560 | B1 | 12/2005 | Healy et al. |
| 6,206,238 | B1 | 3/2001 | Ophardt | 6,974,091 | B2 | 12/2005 | McLisky |
| 6,216,925 | B1 | 4/2001 | Garon | 6,978,914 | B2 | 12/2005 | Furner et al. |
| 6,220,293 | B1 | 4/2001 | Rashidi | 6,978,947 | B2 | 12/2005 | Jin |
| 6,237,812 | B1 | 5/2001 | Fukada | 6,981,499 | B2 | 1/2006 | Anderson et al. |
| 6,249,717 | B1 | 6/2001 | Nicholson et al. | 6,997,349 | B2 | 2/2006 | Blacker et al. |
| 6,254,065 | B1 | 7/2001 | Ehrensperger et al. | 7,000,853 | B2 | 2/2006 | Fugere |
| 6,264,548 | B1 | 7/2001 | Payne, Jr. et al. | 7,011,795 | B2 | 3/2006 | Thompson et al. |
| 6,267,297 | B1 | 7/2001 | Contadini et al. | D519,623 | S | 4/2006 | Wu |
| 6,293,442 | B1 | 9/2001 | Mollayan | 7,032,782 | B1 | 4/2006 | Ciavarella et al. |
| D449,229 | S | 10/2001 | Mohary et al. | D521,621 | S | 5/2006 | Slater |
| 6,296,172 | B1 | 10/2001 | Miller | D535,004 | S | 1/2007 | Furner et al. |
| 6,297,297 | B1 | 10/2001 | Brookman et al. | D535,377 | S | 1/2007 | Caserta et al. |
| 6,347,414 | B2 | 2/2002 | Contadini et al. | D535,378 | S | 1/2007 | Caserta et al. |
| 6,357,726 | B1 | 3/2002 | Watkins | 7,168,273 | B2 | 1/2007 | Neergaard et al. |
| 6,361,752 | B1 | 3/2002 | Demarest et al. | 7,182,227 | B2 | 2/2007 | Poile et al. |
| 6,371,450 | B1 | 4/2002 | Davis et al. | D537,929 | S | 3/2007 | Muderlak et al. |
| 6,390,453 | B1 | 5/2002 | Frederickson et al. | D538,915 | S | 3/2007 | Anderson et al. |
| 6,394,153 | B2 | 5/2002 | Skell et al. | 7,195,139 | B2 | 3/2007 | Jaworski et al. |
| 6,394,310 | B1 | 5/2002 | Muderlak et al. | D539,892 | S | 4/2007 | Caserta et al. |
| D458,359 | S | 6/2002 | Blanchette | D541,400 | S | 4/2007 | Heijdenrijk |
| 6,409,093 | B2 | 6/2002 | Ulczynski et al. | 7,201,294 | B2 | 4/2007 | Carlucci et al. |
| D460,544 | S | 7/2002 | Garcia | D543,461 | S | 5/2007 | Mongeon et al. |
| 6,415,957 | B1 | 7/2002 | Michaels et al. | 7,215,084 | B2 | 5/2007 | Sharrah et al. |
| 6,419,122 | B1 | 7/2002 | Chown | 7,222,758 | B1 | 5/2007 | Scheindel |
| 6,446,583 | B2 | 9/2002 | Vieira | 7,223,361 | B2 | 5/2007 | Kvietok et al. |
| 6,454,127 | B1 | 9/2002 | Suomela et al. | D544,085 | S | 6/2007 | Schriner et al. |
| 6,454,185 | B2 | 9/2002 | Fuchs | D546,434 | S | 7/2007 | Barraclough |
| 6,478,199 | B1 | 11/2002 | Shanklin et al. | D548,317 | S | 8/2007 | Newton et al. |
| D468,627 | S | 1/2003 | Dampney | D548,824 | S | 8/2007 | Christianson |
| 6,510,561 | B1 | 1/2003 | Hammond et al. | D549,572 | S | 8/2007 | Althouse et al. |
| 6,516,796 | B1 | 2/2003 | Cox et al. | D555,472 | S | 11/2007 | Gedanke |
| 6,517,009 | B2 | 2/2003 | Yahav | 7,296,765 | B2 | 11/2007 | Rodrian |
| D471,970 | S | 3/2003 | Gallagher et al. | 7,299,953 | B2 | 11/2007 | McLisky |
| 6,533,141 | B1 | 3/2003 | Petterson et al. | 7,320,418 | B2 | 1/2008 | Sassoon |
| 6,540,155 | B1 | 4/2003 | Yahav | D561,884 | S | 2/2008 | Furner et al. |
| 6,554,203 | B2 | 4/2003 | Hess et al. | D561,885 | S | 2/2008 | Furner et al. |
| 6,567,613 | B2 | 5/2003 | Rymer | D561,886 | S | 2/2008 | Furner et al. |
| D476,070 | S | 6/2003 | Millán | 7,341,169 | B2 | 3/2008 | Bayer |
| 6,588,627 | B2 | 7/2003 | Petterson et al. | 7,365,810 | B2 | 4/2008 | Gotoh et al. |
| RE38,207 | E | 8/2003 | Benoist | 7,407,065 | B2 | 8/2008 | Hooks et al. |
| D478,003 | S | 8/2003 | Bodker et al. | 7,540,433 | B2 | 6/2009 | Fleming et al. |
| D478,379 | S | 8/2003 | Talenton et al. | 7,584,907 | B2 | 9/2009 | Contadini et al. |
| 6,607,102 | B1 | 8/2003 | Griese et al. | 7,610,118 | B2 | 10/2009 | Schramm et al. |
| D479,592 | S | 9/2003 | Lammel et al. | 2001/0020450 | A1 | 9/2001 | Vieira |
| 6,612,464 | B2 | 9/2003 | Petterson et al. | 2002/0020756 | A1 | 2/2002 | Yahav |
| 6,619,562 | B2 | 9/2003 | Hamaguchi et al. | 2002/0074349 | A1 | 6/2002 | Michaels |
| D480,300 | S | 10/2003 | Lee | 2003/0079744 | A1 | 5/2003 | Bonney et al. |
| D480,638 | S | 10/2003 | Lee | 2003/0132254 | A1 | 7/2003 | Giangreco |
| 6,644,507 | B2 * | 11/2003 | Borut et al. ............. 222/37 | 2004/0011885 | A1 | 1/2004 | McLisky |
| D484,585 | S | 12/2003 | Upson | 2004/0028551 | A1 | 2/2004 | Kvietok et al. |
| 6,669,105 | B2 | 12/2003 | Bryan et al. | 2004/0033171 | A1 * | 2/2004 | Kvietok et al. ............. 422/123 |
| 6,688,492 | B2 | 2/2004 | Jaworski et al. | 2004/0035949 | A1 | 2/2004 | Elkins et al. |
| 6,694,536 | B1 | 2/2004 | Haygreen | 2004/0074935 | A1 | 4/2004 | Chon |
| 6,698,616 | B2 | 3/2004 | Hidle et al. | 2004/0155056 | A1 | 8/2004 | Yahav |

| | | | |
|---|---|---|---|
| 2004/0219863 A1 | 11/2004 | Willacy | |
| 2005/0004714 A1 | 1/2005 | Chen | |
| 2005/0067439 A1 | 3/2005 | Fruner | |
| 2005/0201944 A1 | 9/2005 | Kvietok et al. | |
| 2005/0224596 A1 | 10/2005 | Panopoulos | |
| 2006/0011737 A1 | 1/2006 | Amenos et al. | |
| 2006/0037532 A1 | 2/2006 | Eidson | |
| 2006/0060615 A1 | 3/2006 | McLisky | |
| 2006/0076366 A1 | 4/2006 | Furner et al. | |
| 2006/0083632 A1 | 4/2006 | Hammond et al. | |
| 2006/0137619 A1 | 6/2006 | Dodman et al. | |
| 2006/0151546 A1 | 7/2006 | McLisky | |
| 2006/0153733 A1 | 7/2006 | Sassoon | |
| 2006/0175357 A1 | 8/2006 | Hammond | |
| 2006/0191955 A1 | 8/2006 | McLisky | |
| 2007/0036673 A1 | 2/2007 | Selander | |
| 2007/0080172 A1 | 4/2007 | Tyrrell et al. | |
| 2007/0138326 A1 | 6/2007 | Hu | |
| 2007/0158359 A1 | 7/2007 | Rodrian | |
| 2007/0172382 A1 | 7/2007 | Uchiyama et al. | |
| 2007/0199952 A1 | 8/2007 | Carpenter et al. | |

FOREIGN PATENT DOCUMENTS

| | | |
|---|---|---|
| AU | 752399 | 7/2001 |
| DE | 19803696 | 8/1999 |
| DE | 103 92 689 | 4/2005 |
| DE | 103 92 794 | 6/2005 |
| EP | 038 598 | 10/1981 |
| EP | 401060 | 12/1990 |
| EP | 676133 | 10/1995 |
| EP | 757 006 | 2/1997 |
| EP | 1184083 | 3/2002 |
| EP | 1214949 | 6/2002 |
| EP | 1316514 | 6/2003 |
| EP | 1382399 | 1/2004 |
| EP | 1407790 | 4/2004 |
| EP | 1430958 | 6/2004 |
| EP | 1522506 | 4/2005 |
| EP | 1695720 | 8/2006 |
| EP | 1726315 | 11/2006 |
| FR | 2671294 | 1/1991 |
| GB | 2094407 | 9/1982 |
| GB | 2 248 888 | 4/1992 |
| GB | 2305261 | 4/1997 |
| GB | 2375710 | 11/2002 |
| JP | 2002-113398 | 4/2002 |
| JP | 2004-331517 | 11/2004 |
| JP | 2007-246528 | 9/2007 |
| WO | WO 88/05758 | 8/1988 |
| WO | WO 91/15409 | 10/1991 |
| WO | WO 95/19304 | 7/1995 |
| WO | WO 95/29106 | 11/1995 |
| WO | WO 99/34266 | 7/1999 |
| WO | WO 00/47335 | 8/2000 |
| WO | WO 00/64498 | 11/2000 |
| WO | WO 00/64802 | 11/2000 |
| WO | WO 00/75046 | 12/2000 |
| WO | WO 00/78467 | 12/2000 |
| WO | WO 01/07703 | 2/2001 |
| WO | WO 01/21226 | 3/2001 |
| WO | WO 01/26448 | 4/2001 |
| WO | WO 01/66157 | 9/2001 |
| WO | WO 02/40177 | 5/2002 |
| WO | WO 02/40376 | 5/2002 |
| WO | WO 02/072161 | 9/2002 |
| WO | WO 02/079679 | 10/2002 |
| WO | WO 02/087976 | 11/2002 |
| WO | WO 02/094014 | 11/2002 |
| WO | WO 03/005873 | 1/2003 |
| WO | WO 03/037748 | 5/2003 |
| WO | WO 03/037750 | 5/2003 |
| WO | WO 03/042068 | 5/2003 |
| WO | WO 03/062094 | 7/2003 |
| WO | WO 03/062095 | 7/2003 |
| WO | WO 03/068412 | 8/2003 |
| WO | WO 03/068413 | 8/2003 |
| WO | WO 03/086902 | 10/2003 |
| WO | WO 03/086947 | 10/2003 |
| WO | WO 03/099682 | 12/2003 |
| WO | WO 03/104109 | 12/2003 |
| WO | WO 2004/002542 | 1/2004 |
| WO | WO 2004/043502 | 5/2004 |
| WO | WO 2004/110507 | 6/2004 |
| WO | WO 2004/067963 | 8/2004 |
| WO | WO 2004/073875 | 9/2004 |
| WO | WO 2004/081303 | 9/2004 |
| WO | WO 2004/093927 | 11/2004 |
| WO | WO 2004/093928 | 11/2004 |
| WO | WO 2004/105816 | 12/2004 |
| WO | WO 2004/105817 | 12/2004 |
| WO | WO 2004/105818 | 12/2004 |
| WO | WO 2005/001212 | 1/2005 |
| WO | WO 2005/014060 | 2/2005 |
| WO | WO 2005/018691 | 3/2005 |
| WO | WO 2005/023679 | 3/2005 |
| WO | WO 2005/072059 | 8/2005 |
| WO | WO 2005/072522 | 8/2005 |
| WO | WO 2006/012248 | 2/2006 |
| WO | WO 2006/044416 | 4/2006 |
| WO | WO 2006/058433 | 6/2006 |
| WO | WO 2006/064187 | 6/2006 |
| WO | WO 2006/084317 | 8/2006 |
| WO | WO 2006/104993 | 10/2006 |
| WO | WO 2006/105652 | 10/2006 |
| WO | WO 2006/108043 | 10/2006 |
| WO | WO 2007/029044 | 3/2007 |
| WO | WO 2007/045828 | 4/2007 |
| WO | WO 2007/052016 | 5/2007 |
| WO | WO 2007/064188 | 6/2007 |
| WO | WO 2007/064189 | 6/2007 |
| WO | WO 2007/064197 | 6/2007 |
| WO | WO 2007/064199 | 6/2007 |
| WO | WO 2007/132140 | 11/2007 |
| WO | WO 2008/056131 | 5/2008 |

OTHER PUBLICATIONS

Web Page "AirWick FreshMatic" @ http://www.cleanware.co.nz/product_info.php?products_id=159 dated Mar. 7, 2005 (1 page).
Web Page http://www.cleanware.co.nz/images/client/AirWick2.jpg dated Mar. 7, 2005 (1 page).
Web Page "FreshMatic Refill Citrus" @ http://www.cleanware.co.nz/product_info.php?products_id=161 dated Mar. 7, 2005 (1 page).
Web Page "AirWick Frequently Asked Questions" @ http://www.airwick.co.uk/faqs_page/faqs.html dated Mar. 7, 2005 (6 pages).
Web Page "AirWick Personalize Your Atmosphere with the Fragrances You Love" @ http://www.airwick.co.uk/product_page/product.html dated Mar. 7, 2005 (5 pages).
Extended European Search Report for EP Appl. No. 07011131.5-2425 (based on PCT/US2005/036576) dated Aug. 27, 2007.
Extended European Search Report for EP Appl. No. 07011132.3-2425 (based on PCT/US2005/036576) dated Aug. 27, 2007.
PCT/US08/003317 International Search Report and Written Opinion dated Nov. 6, 2008.
Office Action dated Jul. 7, 2010, for U.S. Appl. No. 11/725,402, filed Mar. 19, 2007, inventors Carpenter et al.
PCT/US05/036576 International Preliminary Report on Patentability and Written Opinion of the International Searching Authority dated Apr. 1, 2007.
European Office Action for EP 08 726 782.9-1268 dated Jun. 8, 2010.
Office Action dated Sep. 29, 2010, for U.S. Appl. No. 12/796,473, dated Jun. 8, 2010, inventors Furner et al.

* cited by examiner

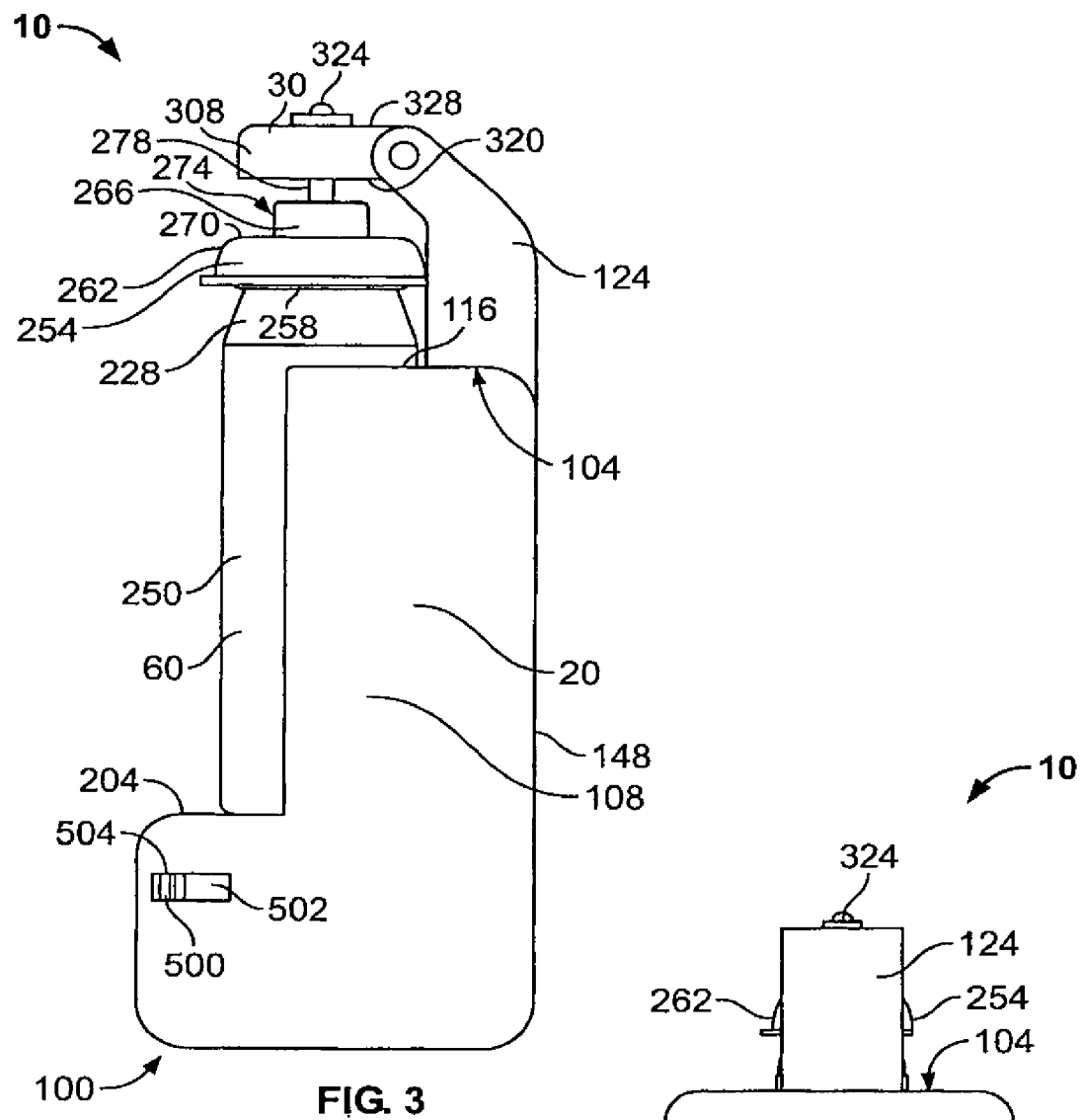
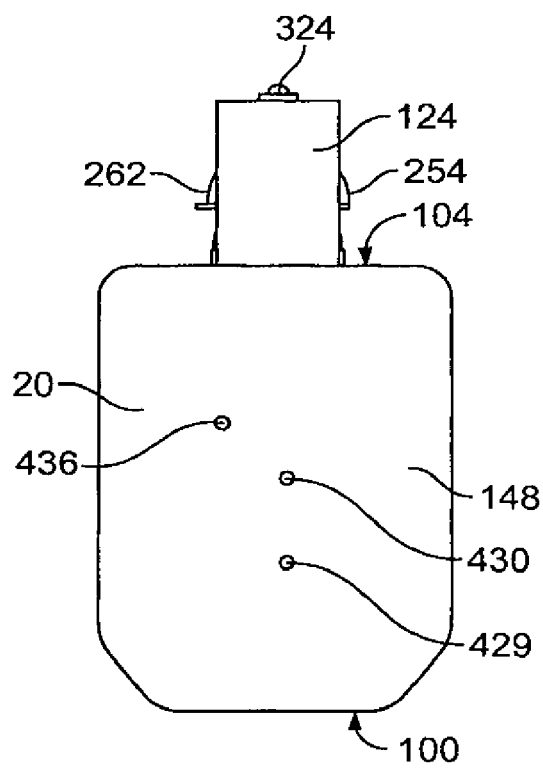
FIG. 3
FIG. 4

COMPACT SPRAY DEVICE

CROSS REFERENCE TO RELATED APPLICATIONS

This application is a divisional of application Ser. No. 11/247,793, filed Oct. 11, 2005 which is now U.S. Pat. No. 7,837,065, which claims the benefit of U.S. Provisional Application Ser. No. 60/617,950, filed Oct. 12, 2004.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present disclosure relates to discharging a fluid from a spray device, and more particularly, to a method and apparatus for discharging a liquid through a nozzle of an aerosol container.

2. Description of the Background

An automatic discharge device for an aerosol container containing a pressurized fluid within a housing typically includes an actuator mechanism for engaging a nozzle of the aerosol container. In a specific example, a motor displaces the actuator mechanism in response to input received from a sensor, wherein the displacement causes the actuator mechanism to engage the nozzle of the aerosol container and discharge the pressurized fluid therefrom.

Hill et al. U.S. Pat. No. 4,544,086 discloses an ornament that includes a valving mechanism for discharging a pressurized fluid from an aerosol can. The valving mechanism comprises an actuator bar that contacts and depresses a nozzle of the aerosol can to release the pressurized fluid therefrom. The released pressurized fluid acts upon a diaphragm within the valving mechanism to force hydraulic fluid from a first chamber into a second chamber, wherein the fluid entering the second chamber raises a piston. The rising piston forces the actuator bar to rise therewith and disengage from the nozzle, thereby terminating fluid discharge from the can. The pressurized fluid within the valving mechanism is thereafter controllably released to permit the piston to drop so that the actuator rod engages the nozzle again.

Lynn U.S. Pat. No. 5,924,597 discloses a fragrance dispensing apparatus for use in a multi-room building having an existing HVAC system ventilated by a forcing fan. The apparatus includes a plurality of fragrance containers, a plurality of solenoids, a plurality of programmable timers, and a single fan timer.

Mollayan U.S. Pat. No. 6,293,442 discloses a timed spray dispenser for distributing a liquid deodorizer from an aerosol can disposed within a housing of the dispenser. A lever arm is pivotably mounted on the housing and includes a first end that engages a spray valve of the can and a second end that engages an eccentric cam, wherein the eccentric cam is rotated by a timer controlled motor. As the eccentric cam is rotated, the cam pivots the lever arm, thereby causing the first end to depress the spray valve and discharge the contents of the can.

Chown U.S. Pat. No. 6,419,122 discloses an apparatus for dispensing a chemical from an aerosol container. The container is provided with a magnetic material and a solenoid coil extending around the container. Energization of the solenoid coil causes the container to move upwardly from a non-dispensing position to a dispensing position.

Borut et al. U.S. Pat. No. 6,644,507 discloses an automatic air freshener that utilizes an electric motor coupled to an actuator cam, wherein a lobe of the actuator cam engages an end of an aerosol canister. The cam causes the canister to slide upwardly through a frame toward a housing aperture, wherein a valve of the canister is depressed within the housing aperture to open the valve and dispense the contents of the canister therefrom.

SUMMARY OF THE INVENTION

According to one embodiment of the present invention, a method of operating a dispensing unit includes the step of providing a power source to a dispensing unit that includes a housing having an aerosol container disposed therein and an actuator arm. Another step includes activating the dispensing unit in response to a minimum threshold of light being sensed by a light sensor. In a different step a sleep period interval between spray operations is selected. Yet another step comprises moving the actuator arm after completion of a startup delay period from a pre-actuation position to a discharge position along a path substantially parallel to an axial length of the container to actuate a nozzle of the container to discharge a fluid from the container. The method also includes the step of alternating automatically between the sleep period having a duration commensurate with the selected sleep period interval and a discharge period during which the fluid is dispensed from the container.

Other aspects and advantages will become apparent upon consideration of the following detailed description and the attached drawings, in which like elements are assigned like reference numerals.

BRIEF DESCRIPTION OF THE DRAWINGS

FIG. 3 is a side elevational view of the dispenser of FIG. 2;

FIG. 4 is a rear elevational view of the dispenser of FIG. 2;

DETAILED DESCRIPTION OF THE DRAWINGS

Figure 1:
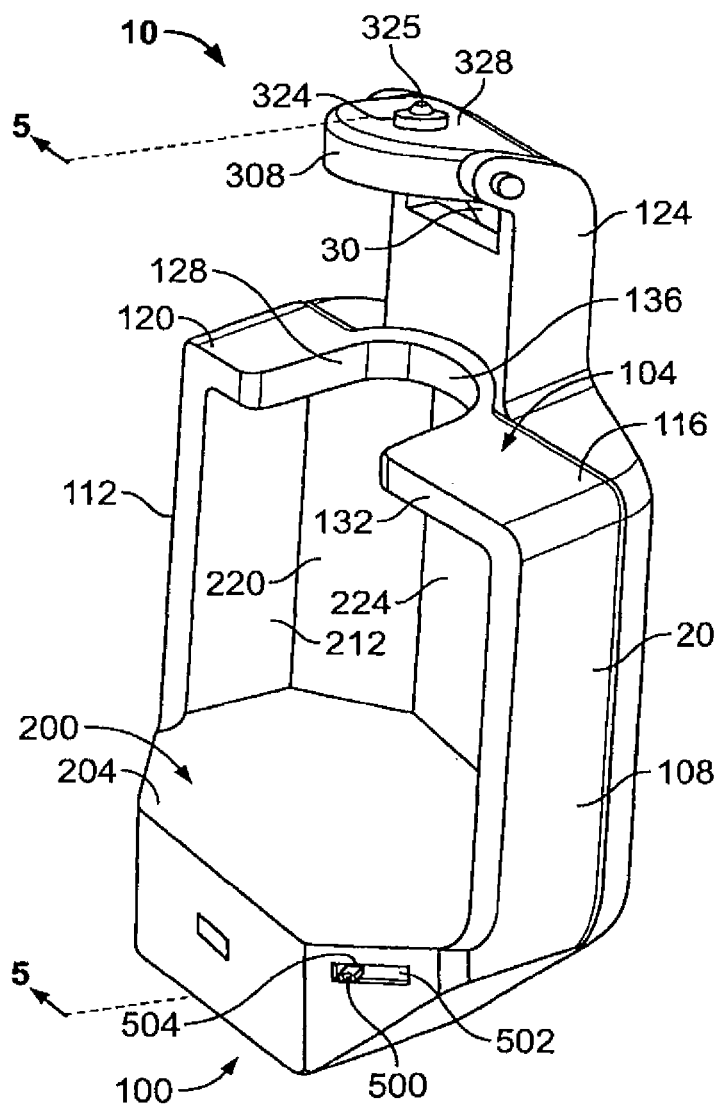
FIG. 1 is an isometric view of one type of dispenser wherein batteries and a fluid container are omitted therefrom.
Figure 2:
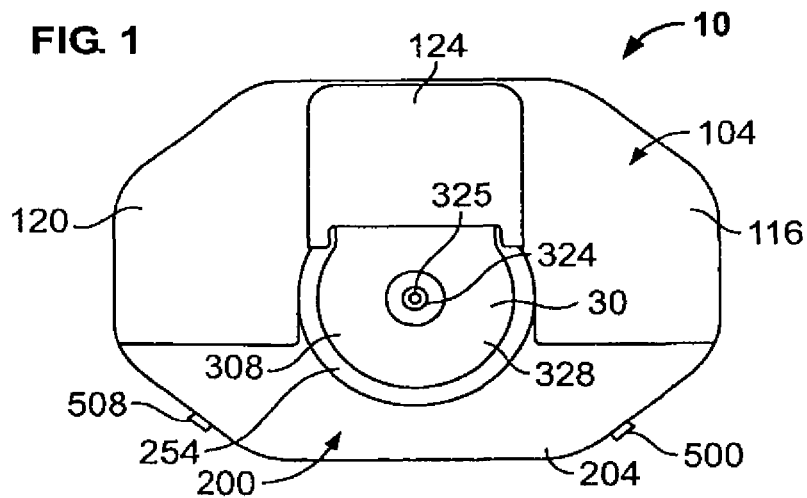
FIG. 2 is a plan view of the dispenser of FIG. 1 with a fluid container inserted therein.

FIGS. 1-6 depict one embodiment of a dispenser 10. The dispenser 10 generally comprises a housing 20, an actuator arm 30, and a drive unit 40. A container 60 is disposed within the housing 20 of the dispenser 10. The dispenser 10 discharges fluid from the container 60 upon occurrence of a particular condition. The condition could be the manual activation of the device or the automatic activation of the device in response to an elapsed time interval or signal from a sensor. The fluid may be a fragrance or insecticide disposed within a carrier liquid, a deodorizing liquid, or the like. For example, the fluid may comprise OUST®, an air and carpet sanitizer for household, commercial, and institutional use, or GLADE®, a household deodorant, both sold by S.C. Johnson and Son, Inc., of Racine, Wis. The fluid may also comprise other actives, such as sanitizers, air fresheners, odor eliminators, mold or mildew inhibitors, insect repellents, and the like, or that have aromatherapeutic properties. The fluid alternatively comprises any fluid known to those skilled in the art that can be dispensed from a container. The dispenser 10 is therefore adapted to dispense any number of different fluid formulations.

The housing 20 of the embodiment depicted in FIGS. 1-6 comprises a base portion 100 and a top portion 104. First and second sidewalls 108, 112, respectively, extend between the base portion 100 and the top portion 104. Further, the top portion 104 includes first and second shoulders 116, 120, respectively, wherein the first shoulder 116 extends inwardly from the first sidewall 108 and the second shoulder 120 extends inwardly from the second sidewall 112. The present embodiment also includes an actuator arm cover 124 that extends upwardly from the top portion 104 to cover the actuator arm 30. In a preferred embodiment, the actuator arm cover 124 is contoured to have a shape similar to that of the actuator arm 30.

Figure 5:
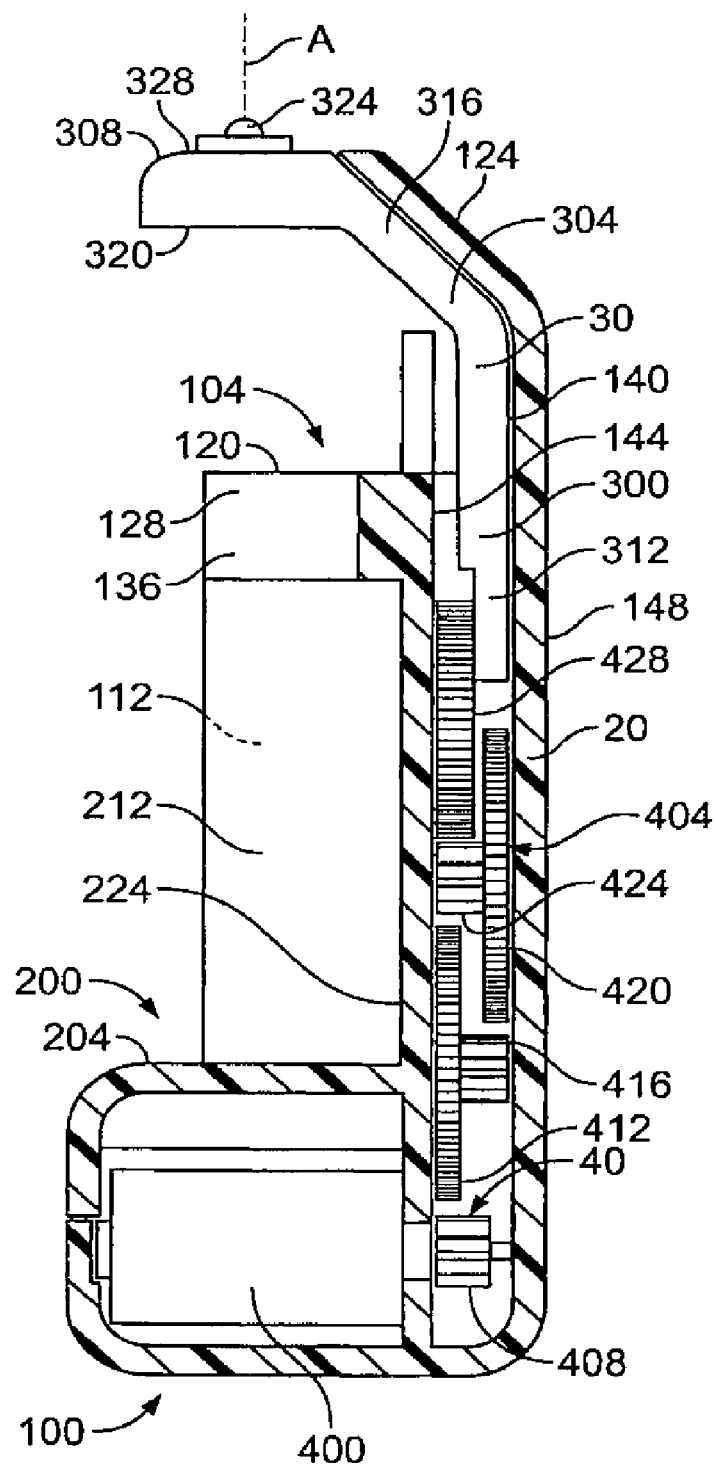
FIG. 5 is a cross-sectional view taken generally along the lines 5-5 of FIG. 1 depicting the dispenser.
Figure 6:
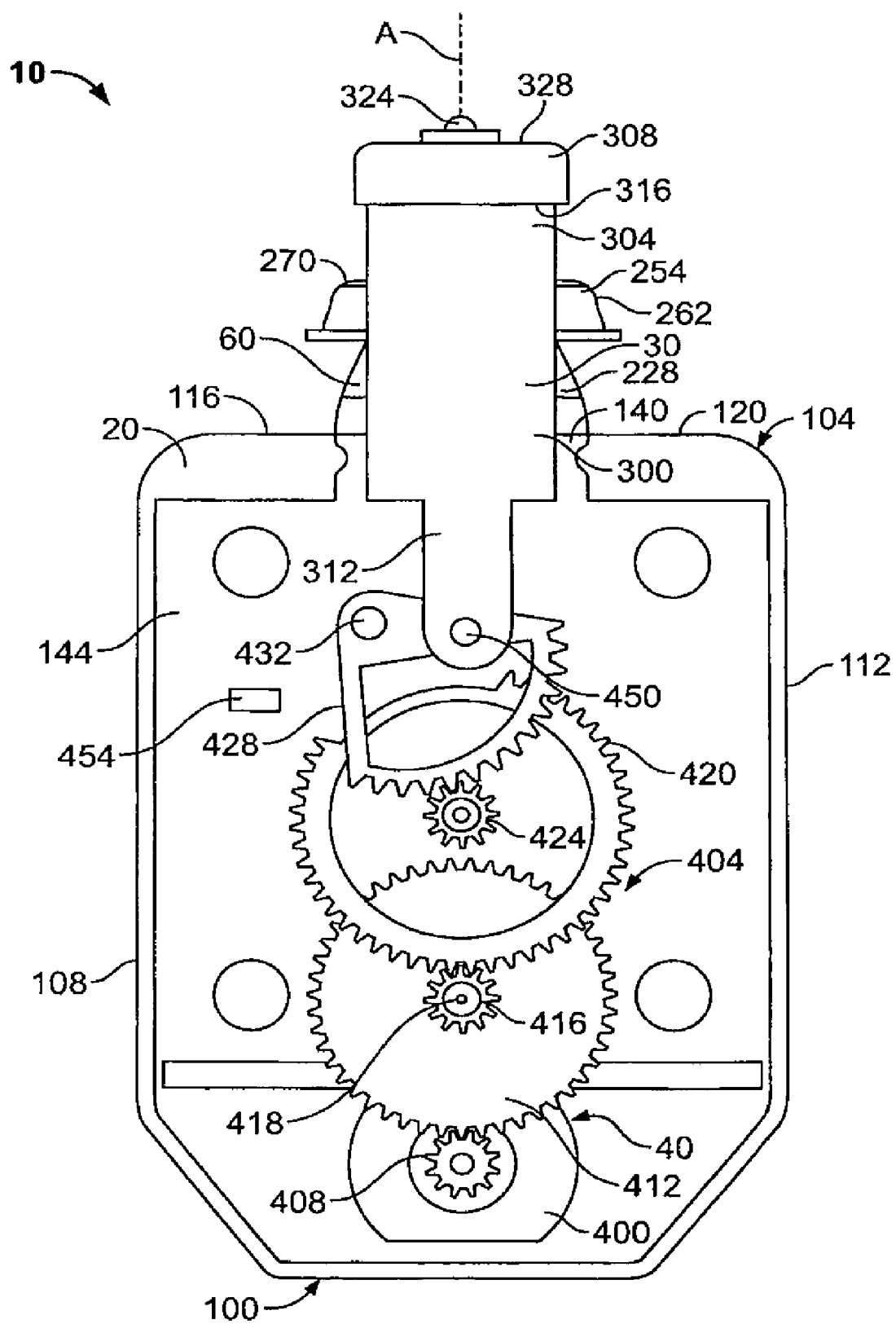
FIG. 6 is a view similar to that of FIG. 4, except that the rear panel of the dispenser is removed to show a drive unit and an actuator arm.

A slot 128 is disposed between the first and second shoulders 116, 120 of the top portion 104 as may be seen in FIG. 1. The slot 128 is substantially cylindrical and is open on a front side 132. An inner wall 136 defining the slot 128 is contoured to allow a portion of the container 60 to easily nest therein. FIGS. 5 and 6 show that the top portion 104 also includes a channel 140 adjacent the slot 128, wherein the channel 140 is disposed between an inner rear panel 144 and an outer rear panel 148 of the housing 20.

With particular reference to FIGS. 1-4, the container 60 is inserted through the front side 132 of the housing 20 and into a recess 200 defined in part by a bottom surface 204, side surfaces 208 and 212, angled surfaces 216 and 220, and a rear surface 224. Further, a neck 228 of the container 60 is inserted into the slot 128, which assists in the alignment and/or securing of the container 60. Two AA batteries 232 are also inserted into the housing 20 through the front side 132 thereof, similar to the embodiment of FIGS. 8 and 9 discussed below. The batteries 232 are secured by an interference fit between respective positive and negative terminals.

The container 60 may be an aerosol container or a pump-type sprayer container of any size and volume known to those skilled in the art. However, the container 60 is preferably an aerosol container comprising a body 250 with a mounting cup 254 crimped to a top end 258 thereof. The mounting cup 254 is generally cylindrical in shape and includes an outer wall 262 that extends circumferentially therearound. In some instances, the neck 228 of the container 60 is disposed below the mounting cup 254, wherein the neck 228 is angled inwardly with respect to the mounting cup 254 and the remaining area of the body 250. A pedestal 266 also extends upwardly from a central portion of a base 270 of the mounting cup 254. A valve assembly 274 within the container 60 includes a valve stem 278, wherein a distal end 282 of same extends through the pedestal 266. If desired, a button or other actuator (not shown) may also be assembled onto the distal end 282 of the valve stem 278. When the distal end 282 of the valve stem 278 is depressed the valve assembly 274 is opened and the contents of the container 60 are discharged through an orifice 286 of the valve stem 278. The contents of the container 60 may be discharged in a continuous or metered dose. Further, the discharging of the contents of the container 60 may be effected in any number of ways, e.g., a discharge comprising a partial metered dose, a discharge through a partial opening of the valve assembly 274, multiple consecutive discharges, etc.

With regard to FIGS. 5 and 6, the actuator arm 30 includes a main portion 300, an intermediate portion 304, and an overhang portion 308. A depending attachment portion 312 that includes a bore extends downwardly from the main portion 300. The attachment portion 312 is coupled to a section of the drive unit 40, as noted in greater detail hereinafter. The main portion 300 is disposed within the channel 140 and is substantially parallel with the outer rear panel 148 of the housing 20. The intermediate portion 304 of the actuator arm 30 extends laterally and upwardly from the main portion 300. An upper end 316 of the intermediate portion 304 is therefore farther from the outer rear panel 148 and the top portion 104 of the housing 20 than the main portion 300. The overhang portion 308 of the actuator arm 30 extends from the upper end 316 of the intermediate portion 304 toward the front side 132 of the housing 20. The overhang portion 308 is substantially transverse to the main portion 300. Further, at least a section of the overhang portion 308 is disposed above the slot 128.

Prior to opening the valve assembly 274 and releasing the contents of the container 60, the actuator arm 30 and overhang portion 308 are positioned in a pre-actuation position. Preferably, when the actuator arm 30 and the overhang portion 308 are disposed in the pre-actuation position, the distal end 282 of the valve stem 278 is spaced slightly from or just in contact with a lower side 320 of the overhang portion 308. Alternatively, at this point, the overhang portion 308 may partially depress the valve stem 278 a distance insufficient to open the valve assembly 274.

A dispensing bore 324 terminating at an orifice 325 is provided within the overhang member 308 that extends from an upper side 328 of the overhang portion 308 to the lower side 320 thereof and allows for fluid communication between the container 60 and the outside atmosphere. While the dispensing bore 324 could have any geometrical shape, FIGS. 1-6 depict that the dispensing bore 324 has a circular cylindrical shape. The dispensing bore 324 preferably has a diameter of about 20 mils. A longitudinal axis A of the dispensing bore 324 is preferably oriented in a direction normal to a plane of the base portion 100 of the housing 20. Thus, the contents of the container 60 are discharged upwardly through the dispensing bore 324 and into the atmosphere when the valve assembly 274 is opened. If desired, the dispensing bore 324 may instead be L-shaped or have any other nonlinear shape to direct the contents of the container 60 in a direction other than upwards. Still further, the cross-sectional shape and/or diameter of the dispensing bore 324, and/or the orifice 286 and/or the orifice 325 may be modified to obtain any desired spray pattern, or to alter the swirling and/or mechanical breakup of the discharged liquid, as should be evident to one of ordinary skill in the art.

The actuator arm 30 depresses the valve stem 278 through motion imparted thereto by the drive unit 40. The drive unit 40 includes a drive motor 400 in association with a reduction gear train 404 as may be seen in FIGS. 5 and 6. The drive motor 400 is mounted within the base portion 100 of the housing 20 beneath the bottom surface 204 of the recess 200. The drive motor 400 includes a motor gear 408, otherwise referred to as a first pinion, which is directed toward the outer rear panel 148 of the housing 20. The motor gear 408 meshes with a drive gear 412, wherein the drive gear 412 includes a second pinion 416 that is rotatable about an axle 418. The second pinion 416 of the drive gear 412 meshes with an idler gear 420, wherein the idler gear 420 includes a third pinion 424 that is rotatable about an axle 426. The third pinion 424 of the idler gear 420 meshes with a lever gear 428. The drive, idler, and lever gears 412, 420, 428, respectively, are disposed between the inner rear panel 144 and the outer rear panel 148 of the housing 20. The axles 418 and 426 are molded extrusions extending from the inner rear panel 144, wherein distal ends thereof extend into holes 429 and 430, respectively, of the outer rear panel 148.

The lever gear 428 rotates about an axle 432 that extends from the inner rear panel 144 to a hole 436 of the outer rear panel 148. The lever gear 428 is further connected to the attachment portion 312 by a pin 450 at a point offset from the axle 432. When the lever gear 428 is rotated via the gear reduction train 404 and the drive motor 400 in a clockwise direction (as seen in FIG. 6), the actuator arm 30 is pulled downwardly toward a discharge position. Conversely, when the lever gear 428 is rotated in a counter-clockwise direction, the actuator arm 30 is pushed upwardly toward the pre-actuation position. A molded rib 454 projecting from the inner rear panel 144 interferes with the lever gear 428 when the actuator arm 30 has been pulled into the discharge position.

The actuator arm 30 is moved to the discharge position by pulling same downwardly to a particular point such that the valve stem 278 is depressed and the valve assembly 274 is opened, thereby allowing discharge of fluid through the valve assembly 274. The particular point is selected to coincide with a partial or full depression of the valve stem 278. Fully depressing the valve stem 278 releases either a full metered discharge or a continuous discharge of the container contents, while partially depressing the valve stem 278 results in a partial metered or partial continuous discharge of the container contents. Preferably, although not necessarily, the actuator arm 30 is held in the discharge position for a length of time (referred to hereinafter as a "spraying period"). The duration of the spraying period could range anywhere from a fraction of a second to one or more seconds. Indeed, if desired, the actuator arm 30 could be held in the discharge position until all of the container contents are exhausted. At the end of the spraying period, the drive motor 400 is deenergized and the spring-biased valve stem moves the actuator arm 30 to the pre-actuation position and terminates further spraying. The movement of the actuator arm 30 back to the pre-actuation position is aided by a bounce effect created by deenergizing the drive motor 400 after the lever gear 428 is in forced contact with the molded rib 454. If desired, the actuator arm 30 may be moved to and from the discharge position multiple times in response to the occurrence of a single condition to provide for multiple sequential discharges. Multiple sequential discharges may be beneficial when a single discharge from a continuously discharging container with a long spraying period is not desired, or when a single discharge from a metered container is insufficient.

The drive unit 40 of the dispenser 10 preferably utilizes a high torque rated motor with higher rpm speed relative to prior art dispensers. In some instances, the drive motor 400 is 5 to 10 times faster than motors used in prior art dispensers. A more energy efficient system is obtained by running the drive motor 400 faster during the depression of the valve stem 278. This increase in efficiency is an unexpected result and is counterintuitive to the teachings of the prior art. Further, by placing a substantial portion of the drive unit 40 between the inner and outer rear panels 144, 148, the size of the dispenser 10 relative to prior art dispensers is significantly reduced. Still further, low-weight materials can be used (for example, the gears and motor pinion may be made of flexible urethane or thermoplastic), so that a low-weight dispenser 10 is obtained. The reduced size and weight permits the dispenser 10 to be placed almost anywhere in a home or business. Still further, the disclosed positioning of the drive unit 40 also has the advantage of making a dispenser 10 that is quieter relative to prior art dispensers. Also, the use of a flexible material or materials for the gears further reduces the noise coming from the drive unit 40.

FIG. 1 shows that the dispenser 10 includes a switch 500. The switch 500 has an off position 502 as seen in FIG. 1 and an on position 504 (to the left as seen in FIG. 1). When the switch 500 is moved to the on position, the dispenser 10 operates in an automatic timed mode of operation as noted in greater detail below in connection with FIG. 7. Depression of a further pushbutton switch 508 (FIG. 2) causes a manual spraying operation to be undertaken. The manual spraying option allows the user to override and/or supplement the automatic operation of the dispenser 10 when so desired.

Figure 7:
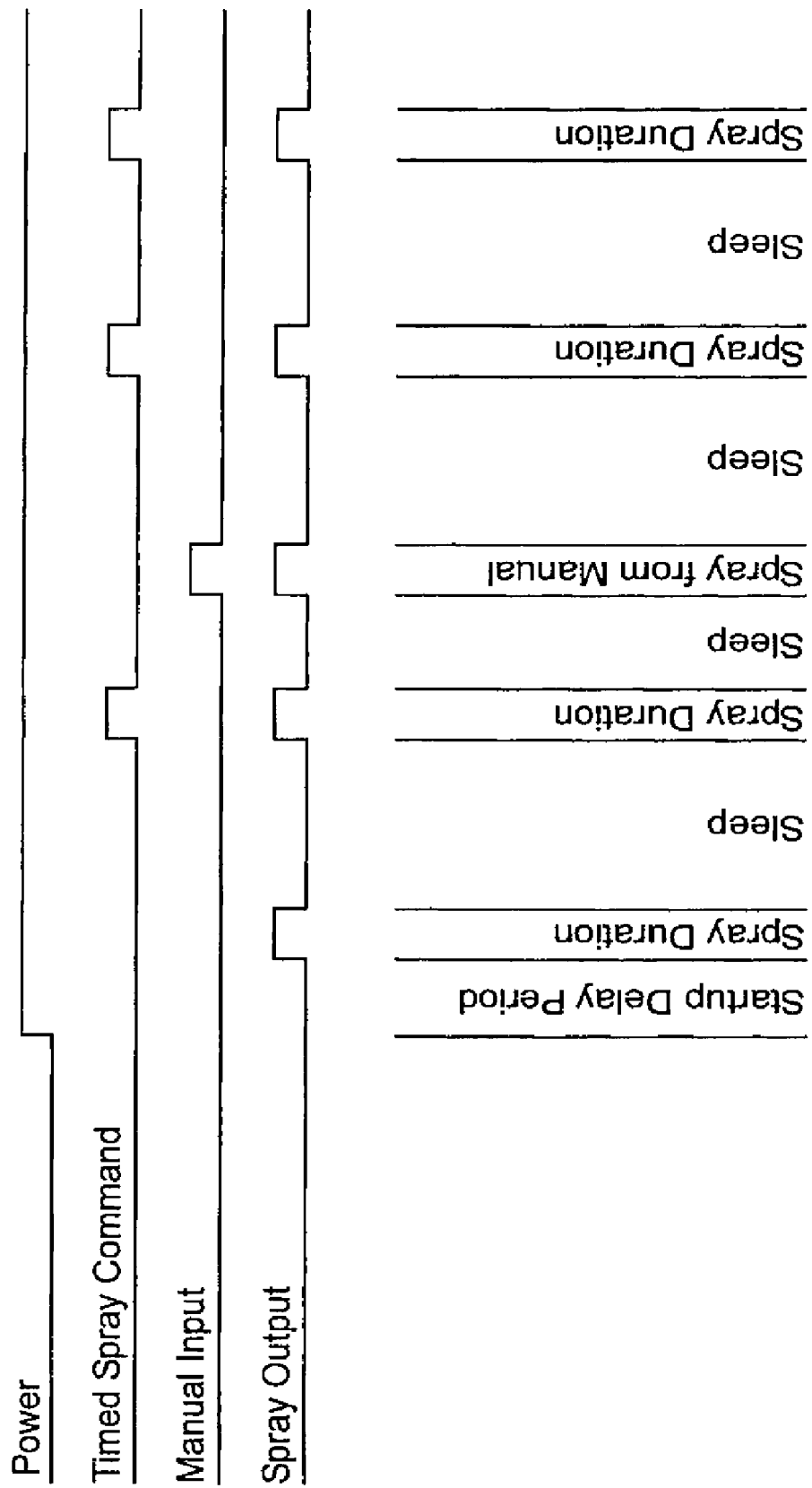
FIG. 7 is a timing diagram illustrating the operation of the dispenser of FIGS. 1-6 according to a first operational sequence.

FIG. 7 depicts a timing diagram of the present embodiment that illustrates operation of the dispenser 10 during use. Initially, the dispenser 10 is energized by moving the switch 500 to the on position whereupon the dispenser 10 enters a startup delay period. Upon completion of the startup delay period, the drive unit 40 is directed to discharge fluid from the dispenser 10 during a first spraying period. The startup delay period is preferably three seconds long. Upon completion of the first spraying period, the dispenser 10 enters a first sleep period that lasts a predetermined time interval, such as about four hours. Upon expiration of the first sleep period the drive unit 40 is actuated to discharge fluid during a second spraying period. Automatic operation thereafter continues with alternating sleep and spraying periods. At any time during a sleep period, the user can manually actuate the dispenser 10 for a selectable or fixed period of time by depressing the pushbutton switch 508. Upon termination of the manual spraying operation, the dispenser 10 initiates a further complete sleep period. Thereafter, a spraying operation is undertaken.

Figure 8:
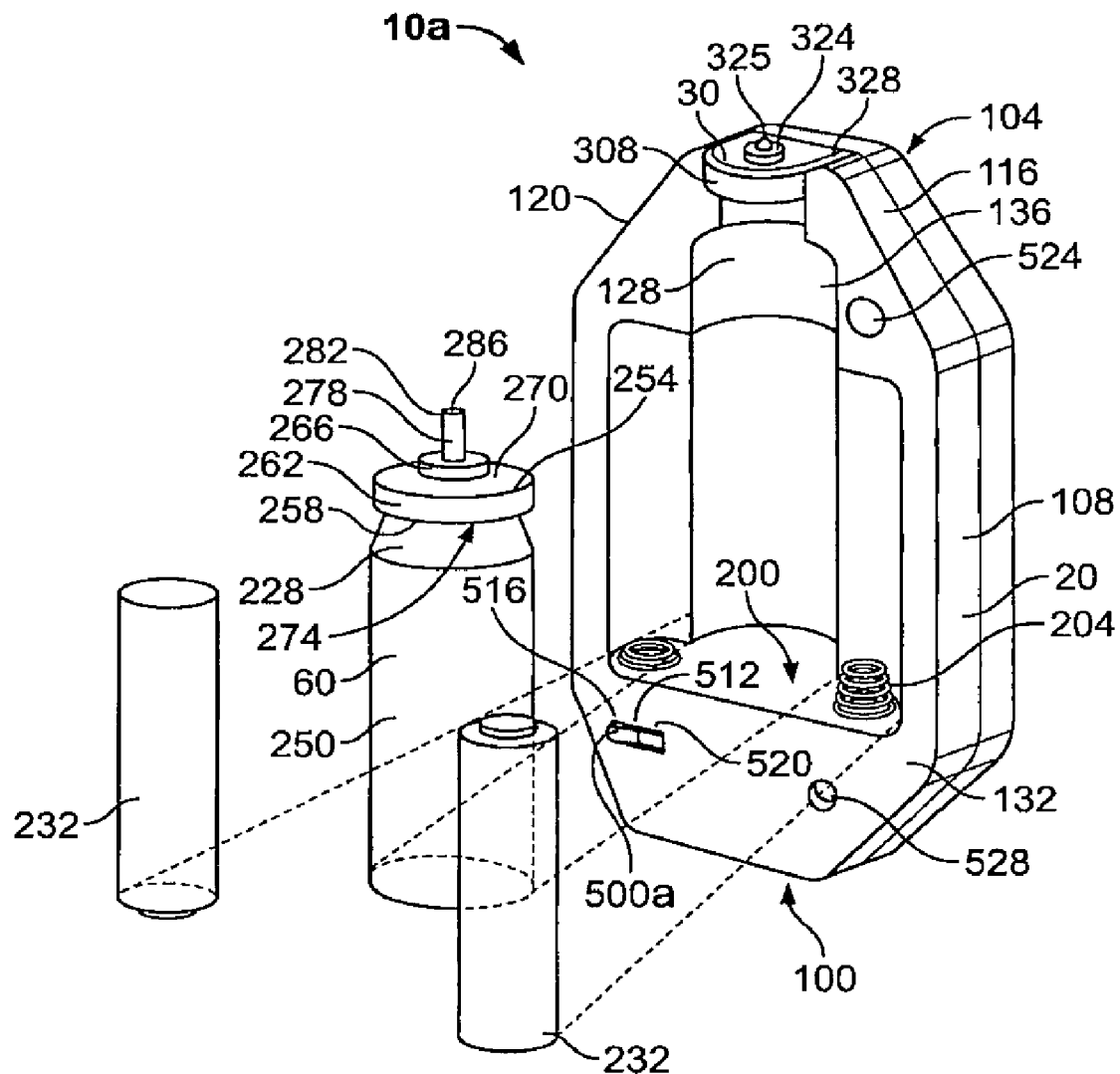
FIG. 8 is an exploded isometric view of another dispenser, an aerosol container, and two batteries.
Figure 9:
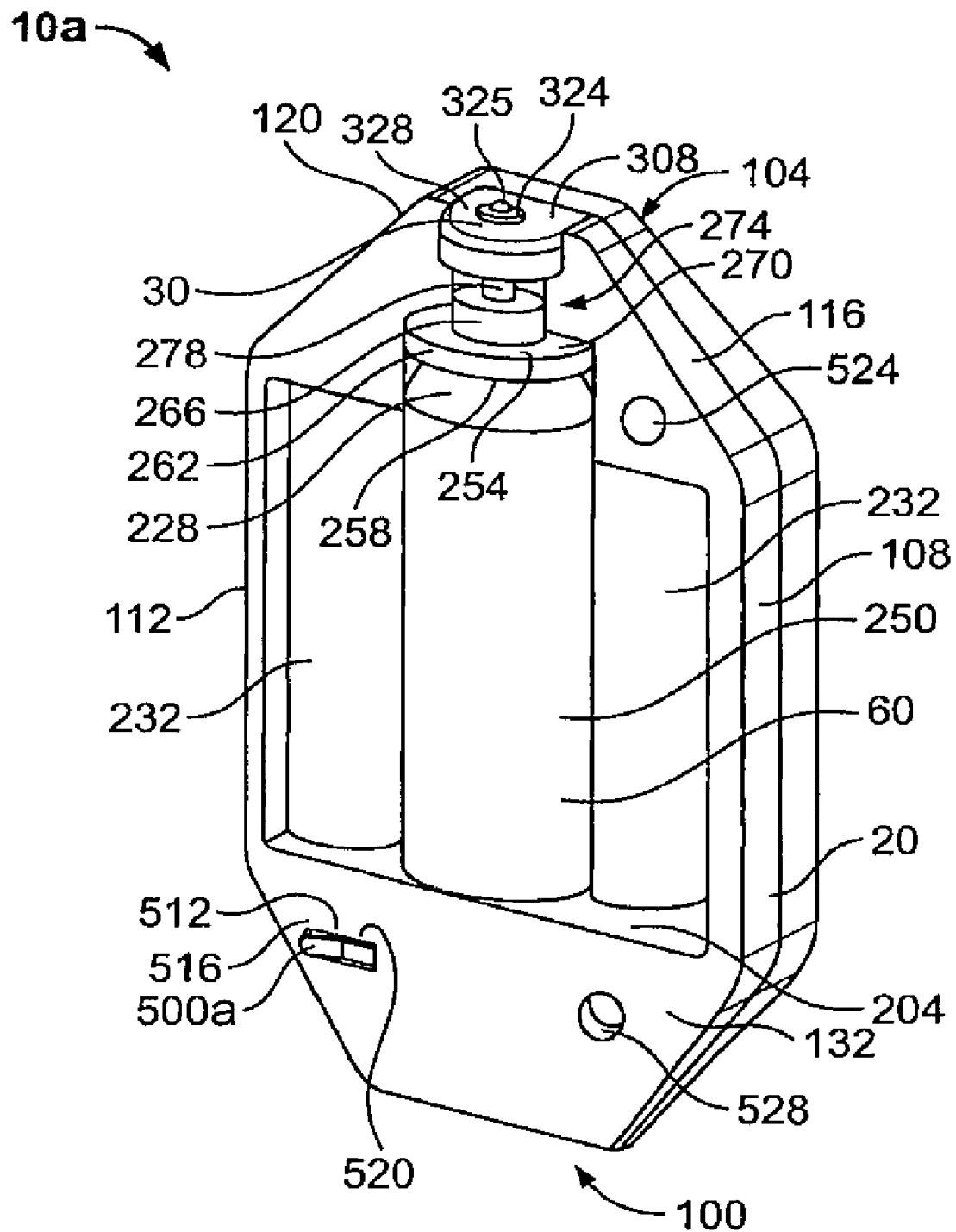
FIG. 9 is an isometric view illustrating the aerosol container and the two batteries placed into the dispenser of FIG. 8.

FIGS. 8 and 9 show another embodiment of a dispenser 10a. A switch 500a is preferably a toggle switch movable to one of three stable positions. When the switch 500a is in a center position 512 the dispenser 10a is deenergized. When the switch 500a is moved to a first on position 516, power is supplied to electrical components of the dispenser 10a and the dispenser 10a operates in a timed mode of operation, as described in connection with FIG. 7 hereinabove. Movement of the switch 500a to a second on position 520 energizes the electrical components of the dispenser 10a and causes the dispenser 10a to operate in a combined timed and sensing mode of operation responsive to the output of a sensor 524, as noted in greater detail hereinafter. A further switch 528 of the push-button type is also provided for manual activation of the drive unit 400, wherein the switch 528 may be depressed by the user to cause a spraying operation at any time, except when the dispenser 10a is off. The switch 528 allows the user to manually override the automated activation of the dispenser 10a.

In the present embodiment, the sensor 524 is a photocell motion sensor. However, other commercially available motion detectors may be utilized with the present embodiment, e.g., a passive infrared or pyroelectric motion sensor, an infrared reflective motion sensor, an ultrasonic motion sensor, or a radar or microwave radio motion sensor. The photocell collects ambient light and allows a controller 532 (FIG. 11) to detect any changes in the intensity thereof. Filtering of the photocell output is undertaken by the controller 532. If the controller 532 determines that a threshold light condition has been reached, e.g., a predetermined level of change in light intensity, the controller 532 activates the drive unit 40. For example, if the dispenser 10a is placed in a lit bathroom, a person walking past the sensor 524 may block a sufficient amount of ambient light from reaching the sensor 524 to cause the controller 532 to activate the dispenser 10a and discharge a fluid.

Figure 10:
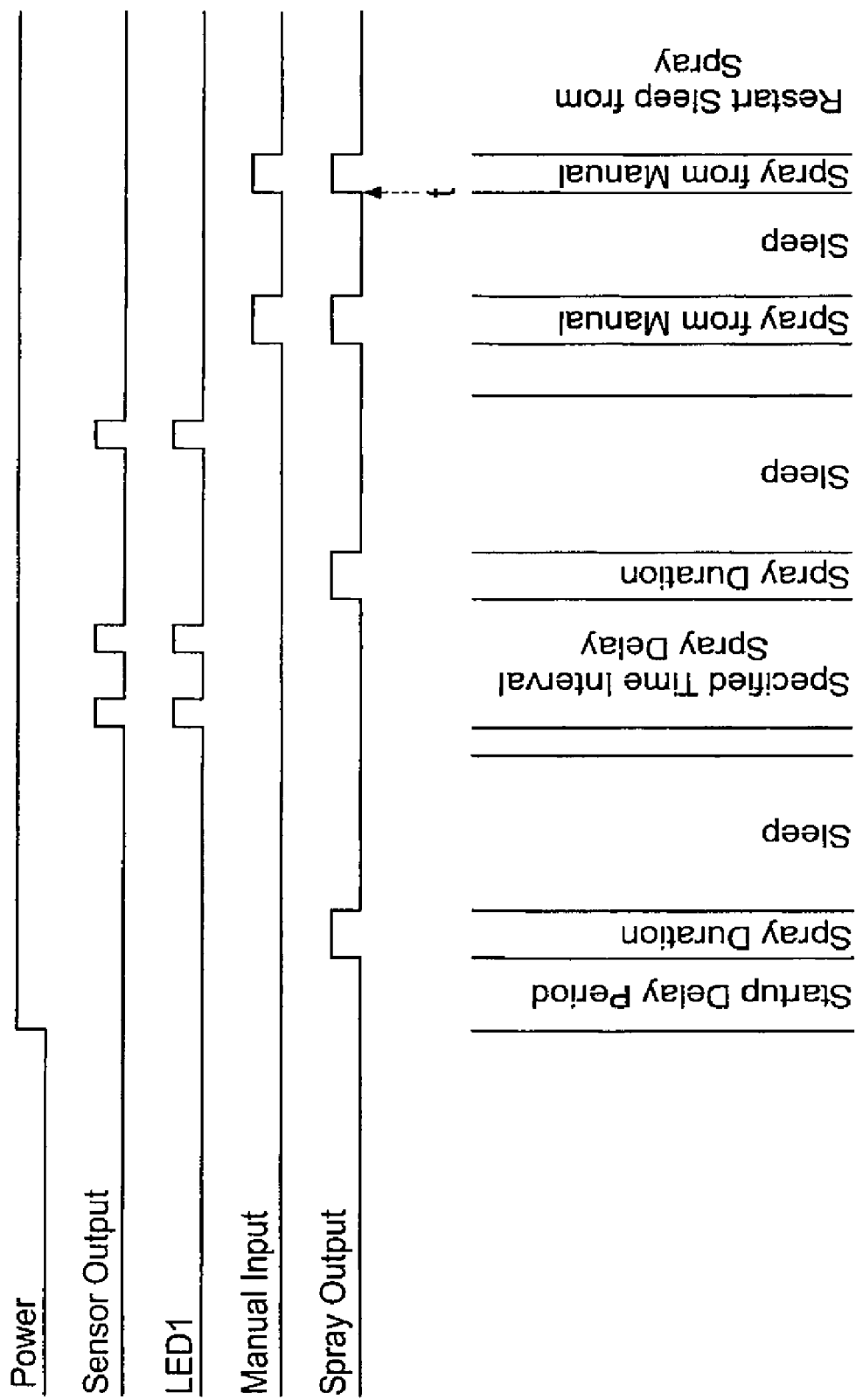
FIG. 10 is another timing diagram illustrating the operation of the dispenser of FIGS. 8 and 9 according to a second operational sequence.

When the switch 500a is moved to the second on position 520, the dispenser 10a preferably operates as shown by the timing diagram of FIG. 10. Moving the switch 500a to the second on position 520 initially causes the dispenser 10a to enter a startup delay period. Upon expiration of the startup delay period, fluid is discharged from the dispenser 10a during a first spraying period. Upon completion of the first spraying period, the dispenser 10a enters a first sleep mode, during which spraying is prevented, even if motion is detected by the sensor 524. Thereafter, if the sensor 524 detects motion after expiration of the first sleep period and sends a sensor output signal to a controller 532, the controller 532 times a specified time interval. The specified time interval is preferably approximately two minutes long. Once the specified time interval has elapsed, the dispenser 10a discharges fluid during a second spraying period. The delay in spraying causes the dispenser 10a to wait the specified time interval following detection of motion to spray the fluid so that the occupant of the room has time to move away from the dispenser 10a and/or leave the room. Upon completion of the second spraying period, the dispenser 10a enters a second sleep period. The dispenser 10a is prevented from automatically activating again in response to detection of motion until the second sleep period has elapsed. The sleep periods prevent over-spraying by numerous automatic activations that may occur in heavily trafficked areas. It is preferred that each sleep period last about one hour.

At any time the user can initiate a manual spraying operation by manually actuating the switch 528 to discharge fluid during a manual spraying period. Upon completion of the manual spraying period, the dispenser 10a undergoes a complete sleep period. Thereafter, the dispenser 10a alternates between sleep periods and spray periods initiated by motion detection following expiration of a sleep period. A full sleep period follows every spray period, regardless of whether the spray period was responsive to motion detection or actuation of the switch 528. For example, the timing diagram of FIG. 10 illustrates another manual actuation at a time t and the dispenser 10a thereafter entering a full sleep period.

In any of the embodiments disclosed herein, the sleep periods may all be of the same duration and a sleep period is automatically undertaken following termination of a spray operation, whether the spray operation is initiated manually or automatically. Also in the preferred embodiments, the lengths of the spray periods are all equal. If desired, one or more of the sleep periods may be longer or shorter than other sleep periods and/or one or more of the spray periods may be longer or shorter than other spray periods. In addition, the startup delay period may be omitted and the first spraying operation can be undertaken immediately upon power-up of the dispenser. Still further, the control methodology can be modified to cause spraying operations to be periodically undertaken at equal or unequal intervals without regard to whether a manual spraying operation has been undertaken.

If desired, the dispenser 10a may be modified to be operable only during particular hours, e.g., during the day or only at night.

In a different embodiment, the sensor 524 is a vibration or tilt sensor known to those skilled in the art. By placing the dispenser 10a on a door or a toilet bowl, the closing or flushing of same, respectively, causes the sensor 524 to develop an output signal that is delivered to the controller 532. Thereafter, the dispenser 10a discharges fluid in a manner similar to that described above.

It is also envisioned that numerous other types of sensors 524 could be used with the presently disclosed dispenser 10a. More specifically, a sound activated sensor could activate the dispenser 10a upon or following detection of a sound, such as a toilet flushing or a door closing. Alternatively, a water level sensor may be particularly useful to activate the dispenser 10a when a toilet is flushed or at a certain time following flushing. In a different embodiment, the sensor 524 is a pressure sensor that activates the drive unit 40 at or following the time that a person steps on a specified area of a floor or sits on a toilet seat. In yet another embodiment, a humidity sensor activates the dispenser 10a at or following the time when a toilet is flushed (thereby causing humidity in the vicinity of the toilet to increase) or when the air is too dry or too moist. Still further, a temperature sensor that registers changes in ambient temperature in the vicinity of a toilet may be provided to activate the dispenser 10a at or following the time when a person is near the toilet and thereby raises the ambient temperature in the vicinity thereof. Such a temperature sensor could instead be disposed in a manner to sense temperature change when the water level of a toilet changes so that the dispenser 10a is activated when the toilet is flushed (or at a particular time following flushing). Finally, an odor sensor could detect certain molecules in areas such as a bathroom or kitchen and activate the dispenser 10a immediately or at a particular time following such detection. While it is preferred that only one of the sensors 524 be utilized, any combination of such sensors could be used, with the varying combinations being selected by an appropriate switch or switches. Further, the present listing of potential sensors 524 is not exhaustive but is merely illustrative of the different types of sensors 524 that can be used with the dispenser 10 described herein. Still further, the placement of the dispenser 10 is not confined to any of the specific examples described above. It is intended that the dispenser 10 be placed in any area where the dispensing of a fluid is required and/or where the sensor 524 is effective.

Figure 11:
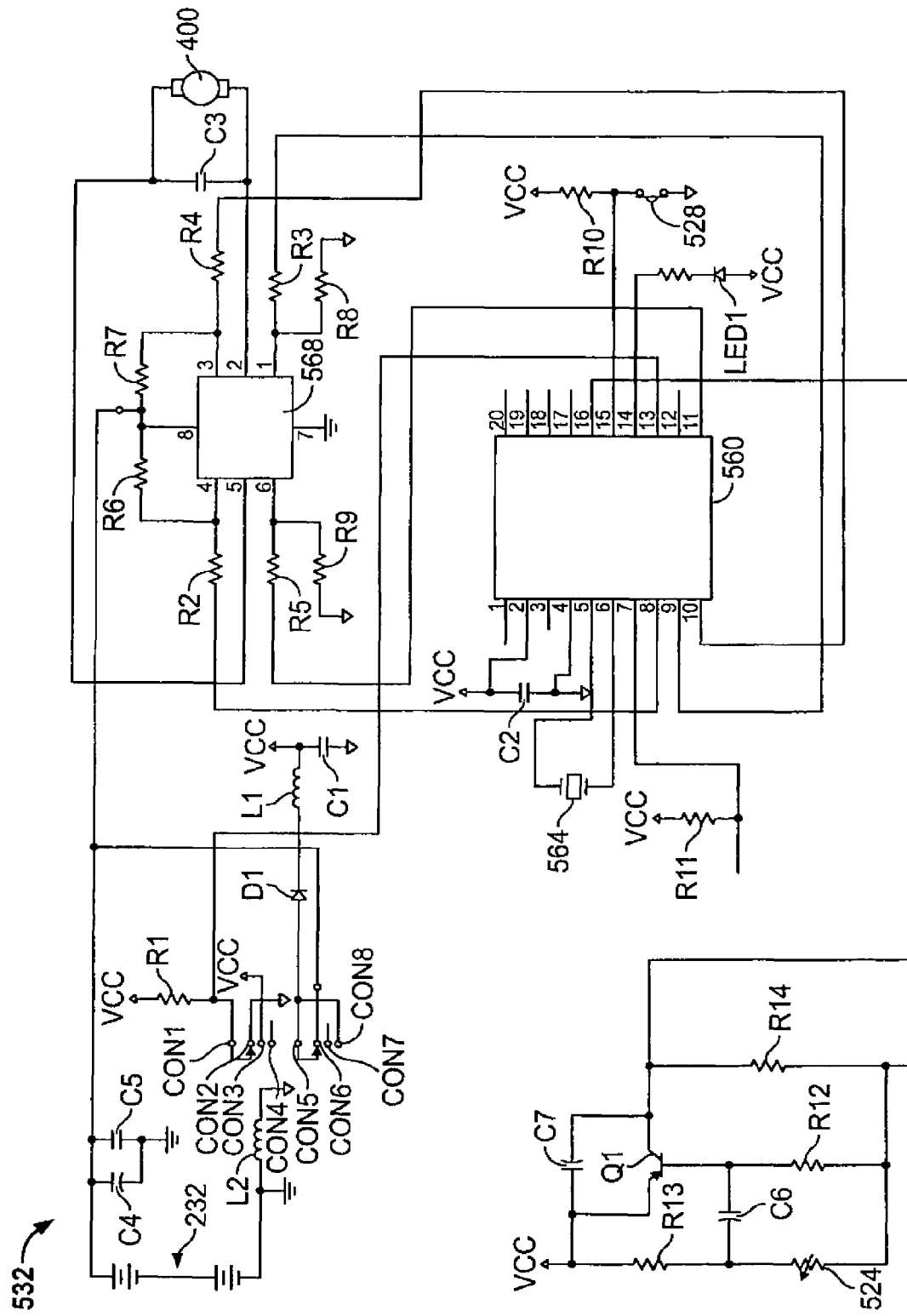
FIG. 11 is a schematic diagram showing an electrical circuit for controlling the motor of any of the dispensers disclosed herein.

Referring next to FIG. 11, a circuit for implementing the controller 532 includes an MSP43OF1121 microprocessor 560 manufactured by Texas Instruments. The integrated circuit 560 is actuable by the switch 500a. More specifically, the switch 500a is of the two-pole, three-throw type and includes contacts CON1-CON8. When the switch 500a is in the middle or off position, contacts CON2 and CON3 are connected to one another as are contacts CON6 and CON7. Accordingly, no power is supplied to the contact CON5 or the contact CON8, and hence, the various components illustrated in FIG. 11, including the integrated circuit 560, are off. When the user moves the switch 500a to the first on position, the contacts CON2 and CON4 are connected to one another as are the contacts CON6 and CON8. The contact CON6 is connected to the positive terminal of series-connected batteries 232, and thus is at a potential of approximately three volts above ground. This voltage is delivered through the contact CON8, a diode D1, and an inductor L1 to develop a voltage VCC. A capacitor C1 is connected between the voltage VCC and ground. The LC circuit formed by the inductor L1 and the capacitor C1 smooth voltage variations so that the voltage VCC remains at a substantially constant level. The voltage VCC is applied to a pin 2 of the integrated circuit 560. Further, ground potential is supplied to a pin 4 of the integrated circuit 560. A capacitor C2 is coupled between the pin 2 and the pin 4 of the integrated circuit 560.

A crystal 564 is connected between a pin 5 and a pin 6 of the integrated circuit 560. The crystal 564 establishes a time base for an internal clock of the integrated circuit 560.

A pin 13 of the integrated circuit 560 is connected to the contact CON1 and a first end of a resistor R1 wherein a second end of the resistor R1 receives the voltage VCC. Pins 8-11 of the integrated circuit 560 are coupled through resistors R2-R5 to pins 4, 1, 8, and 3, respectively, of a further integrated circuit 568, comprising a ZHB6718 SM-8 Bipolar Transistor H-Bridge integrated circuit sold by Zetex PLC of the United Kingdom. Resistors R6 and R7 are connected between the pins 4 and 8, respectively, of the integrated circuit 568 and the positive terminal of the series-connected batteries 232. The pins 1 and 3 of the integrated circuit 568 are connected by resistors R8 and R9, respectively, to ground. In addition, the positive terminal of the series-connected batteries 232 and ground are coupled to pins 6 and 2, respectively, of the integrated circuit 568. Pins 5 and 7 of the integrated circuit 568 are coupled to first and second terminals of the drive motor 400. A capacitor C3 is coupled across the drive motor 400.

A pin 15 of the integrated circuit 560 is connected to a junction between a resistor R10 and the second switch 528. The resistor R10 and the switch 528 are connected between the voltage VCC and ground.

In addition to the foregoing, a negative terminal of the series-connected batteries 232 is connected through an inductor L2 to ground. The integrated circuit 560 can be reset by applying a low state signal to a pin 7. A resistor R11 is connected between the pin 7 and the voltage VCC. A pair of capacitors C4 and C5 are connected between positive and negative terminals of the series-connected batteries 232.

When the switch 500a is in the second on position, a high state signal is supplied to the pin 13 of the integrated circuit 560, thereby causing operation in the timed mode as shown in FIG. 7. This high state signal instructs the integrated circuit 560 to begin the startup delay period. Upon expiration of the startup delay period, appropriate signals are developed at the pins 8-11 of the integrated circuit 560 at the beginning of the first spray period to cause the integrated circuit 568 to energize the drive motor 400 in a first direction. The drive motor 400 rotates the motor gear 408, in turn rotating the gears 412, 420, and 428, thereby moving the actuator arm 30 downwardly. This downward movement depresses the valve stem 278 of the container 60, thereby causing a spraying operation. This motor energization continues for a predetermined amount of time, at the end of which the signals developed at the pins 8-11 of the integrated circuit 560 change to opposite states. The integrated circuit 568 then energizes the drive motor 400 in a second direction, thereby reversing the downward force on the actuator arm 30 and the valve stem 278 of the container 60. The actuator arm 30 and the valve stem 278 then move upwardly in response to upward movement of the arm 30 and the upward force provided by the valve stem 278 so that further release of the contents of the container 60 is prevented.

Following the termination of spraying during the first spray period, the integrated circuit 560 enters the first sleep period. During this time low state signals are developed at the pins 8-11 of the integrated circuit 560 so that the drive motor 400 is kept in an off condition. Upon expiration of the first sleep period, the integrated circuit 560 again develops appropriate signals at the pins 8-11, thereby causing the integrated circuit 568 to energize the drive motor 400. As before, the actuator arm 30 and the valve stem 278 move downwardly, thereby discharging a spray of liquid from the container 60. At the end of this second spraying period, the integrated circuit 560 again develops opposite signals at the pins 8-11, thereby moving the arm 30 upwardly until an end-of-travel limit is reached, whereupon the signals at the pins 8-11 of the integrated circuit 560 all revert to a low state. The drive motor 400 is thus deenergized via the integrated circuit 568 and the integrated circuit 560 prevents further spraying until the expiration of the second sleep period. The integrated circuit 560 thereafter alternates between further spraying and sleep periods as noted above.

At any time during any of the sleep periods, a user can command manual spraying of the container 60 by depressing the switch 528. This action causes a signal developed at the pin 15 of the integrated circuit 560 to transition from a high state to a low state. When this transition is detected, the integrated circuit 560 energizes the drive motor 400 via the pins 8-11 and the integrated circuit 568. At the termination of the spraying operation, the integrated circuit 560 begins timing of a further sleep period, following which a spraying operation is again undertaken.

When the switch 500a is moved to the second on position, a high state signal is provided to the pin 13 of the integrated circuit 560, thereby causing the integrated circuit 560 to enter the combined timed/sensor mode of operation. In this mode of operation, the first spraying operation is undertaken following a startup delay period and a sleep period is initiated at the end of the spraying operation, as seen in FIG. 10.

As seen in FIG. 11, a motion detector circuit 570 includes the sensor 524 in the form of a photoresistor coupled between ground and a first end of an AC coupling capacitor C6. A second end of the capacitor C6 is coupled to a base electrode of a PNP bipolar transistor Q1. The base of the transistor Q1 is coupled to a first end of a biasing resistor R12. A second end of the biasing resistor R12 is coupled to ground. A further resistor R13 is coupled between an emitter electrode of the transistor Q1 and the photoresistor 524. A capacitor C7 is coupled across the emitter electrode and a source electrode of the transistor Q1. A resistor R14 is coupled between the source electrode and ground.

The resistor R13 and the photoresistor 524 act as a voltage divider. The changing resistance of the photoresistor 524 in response to changing light conditions causes a varying voltage to be developed at the junction between the resistor R13 and the photoresistor 524. An AC component of this varying voltage is delivered to the base electrode of the transistor Q1. The transistor Q1 is operated in the linear mode and the components C7 and R14 act as a low-pass filter. The component values are selected so that a signal is developed on a line 572 for each transition in light received by the photoresistor 524 occurring over a short interval. Thus, a signal is developed on the line 572 when a person passes in front of the photoresistor and again when the person moves sufficiently to unblock the photoresistor. No signal is developed on the line 572 when the light transition is developed over a long period of time, such as at dusk or dawn. Each time a signal is developed on the line 572, the integrated circuit 560 pulls the pin 14 thereof to a low voltage for a brief period of time, such as 0.25 second, to energize a light emitting diode LED1 (also seen in the embodiment of FIG. 12). The integrated circuit 560 uses either a high-to-low transition or a low-to-high transition in the signal on the line 572 as a trigger to cause a spraying operation, either immediately or after a delay period, provided that the circuit 560 is not in the sleep mode. The controller 532 operates in accordance with the timing diagram of FIG. 10 during this mode of operation.

Figure 12:
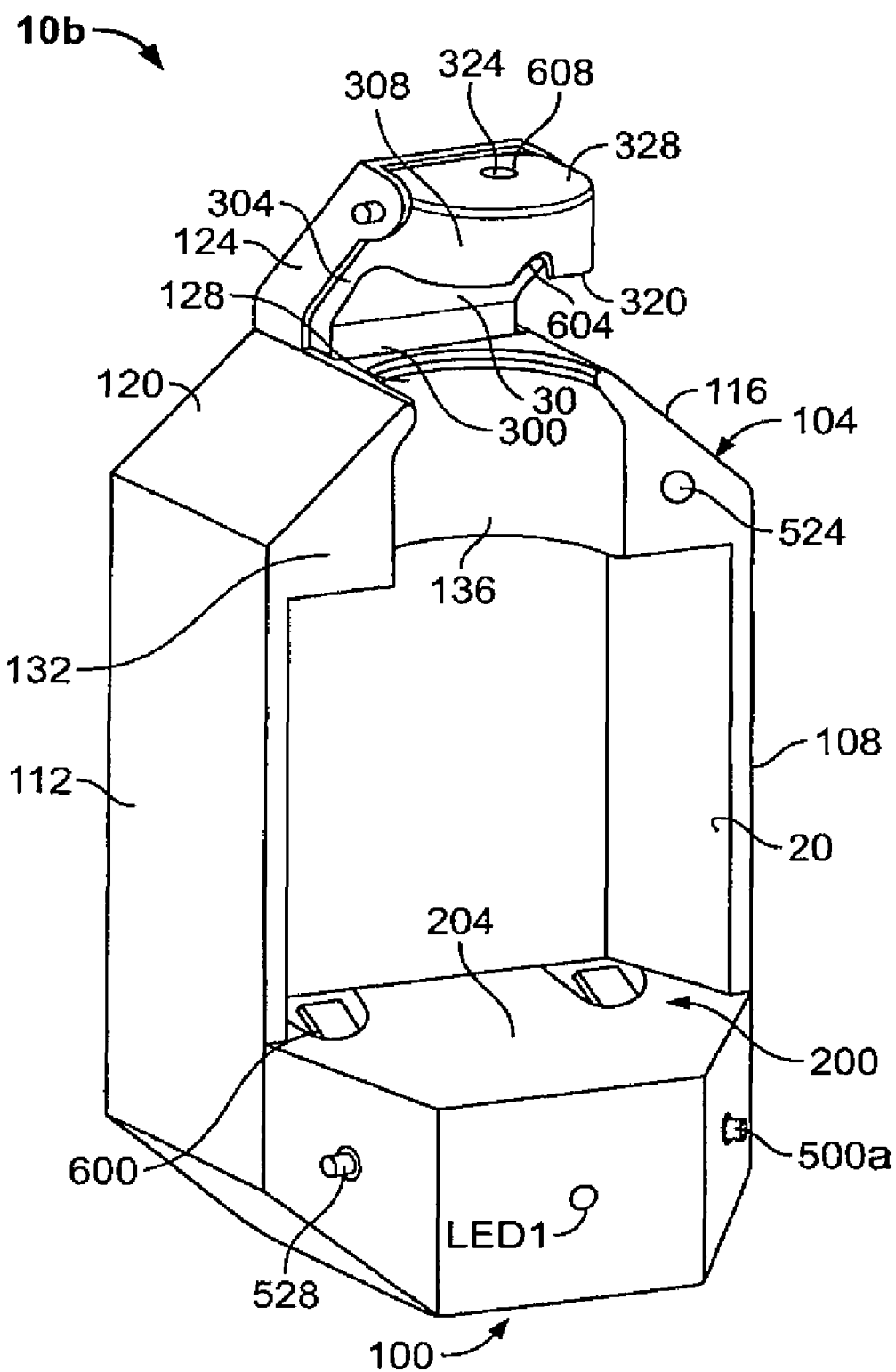
FIG. 12 is an isometric view of yet another dispenser.

FIG. 12 shows another embodiment incorporating the controller 532 and which is identical to the embodiment of FIGS. 8 and 9, except as noted below.

The embodiment of FIG. 12 includes two slots 600 disposed within the bottom surface 204 of the recess 200. The batteries 232 (not shown in FIG. 12) are secured by way of an interference fit between terminals within the two slots 600 and respective terminals on an opposing wall of the recess. The embodiment of FIG. 12 also includes a groove 604 within the overhang portion 308. The groove 604 faces the front side 132 of the housing 20 and is dimensioned to receive the valve stem 278 therein. The present embodiment further includes a recess (not shown) disposed on the lower side 320 of the overhang portion 308. The recess is sufficiently sized to allow entry of a portion of the distal end 282 of the valve stem 278. The recess acts as a centering mechanism to align the valve stem 278 with the second orifice 324 and/or as a directional guide for the discharged contents. A second recess 608 is disposed on the opposite side of the overhang portion 308. The recess 608 may have a cross-sectional size larger than the size of the dispensing bore 324. Further, the cross-sectional size of the recess 608 may vary, e.g., the recess 608 may have a circular shape with a diameter that is smaller adjacent the dispensing bore 324 than the diameter of the recess 608 adjacent the opposite side of the overhang portion 308. When the valve stem 278 is depressed by the downward motion of the overhang portion 308, the fluid dispensed from the container 60 traverses the recess, the dispensing bore 324, and the second recess 608 before being discharged into the atmosphere. The dispensing bore 324 and/or the second recess 608 may discharge the fluid in a direction normal to an axial length of the container 60 or at any angle therefrom.

With regard to the embodiments depicted in FIGS. 1-6, 8, 9, and 12, the dispensers 10, 10a, and 10b may have numerous varying characteristics. For example, the overhang portion 308 or the actuator arm 30 may impart a force onto any area of the valve stem 278 to depress or tilt same.

If desired, the slot 128 may be dimensioned to form an interference fit with the container 60. In yet another alternative, a portion of the container 60, such as the upper portion, is provided with a groove, protrusion, or any other engaging mechanism for interaction with a complementary protrusion, groove, or engaging mechanism, respectively, located on or within the inner wall 136 or any other wall of the dispenser. Further, the inner wall 136 may be angled or tapered inwardly (i.e., toward a center of the slot 128) from bottom to top. The tapering of the inner wall 136 provides for an engagement surface with the neck 228 or any other engagement member of the container 60. Some of the engaging mechanisms assist in keeping the container 60 within the recess 200 and in alignment with the actuator arm 30. Other engaging mechanisms allow for a broader spectrum of container sizes to be used with a single dispenser. For example, a dispenser that has an engaging mechanism for interaction with the neck of a container could hold and align a container having a bottom end thereof in contact with the bottom surface 204 of the recess 200, or a bottom end thereof suspended above the bottom surface 204 of the recess 200.

As a still further alternative, the motor 400 may be driven in two directions to open and close the valve assembly 274. In this case, when spraying is to be terminated, the motor is energized in a second direction to reverse the downward force on the actuator arm 30 and the valve stem 278. The actuator arm 30 and the valve stem 278 then move upwardly to the pre-actuation position in response to upward movement of the actuator arm 30 and the upward force provided by the valve assembly 274, at which time the valve assembly 274 of the container 60 is closed.

In yet another alternative, the axles 418, 426, and 432 are not molded into the inner rear panel 144. Instead, the axles 418, 426, and 432 are mounted into a steel or metal plate, wherein the axles 418, 426, and 432 cantilever from the plate to provide support and alignment.

It is also envisioned that different alternatives of the dispenser may have the ability to hold and spray one or more containers having the same or different products. Further, the dispenser could spray the contents of the containers at the same time or at selected intervals and sequences.

Figure 13:
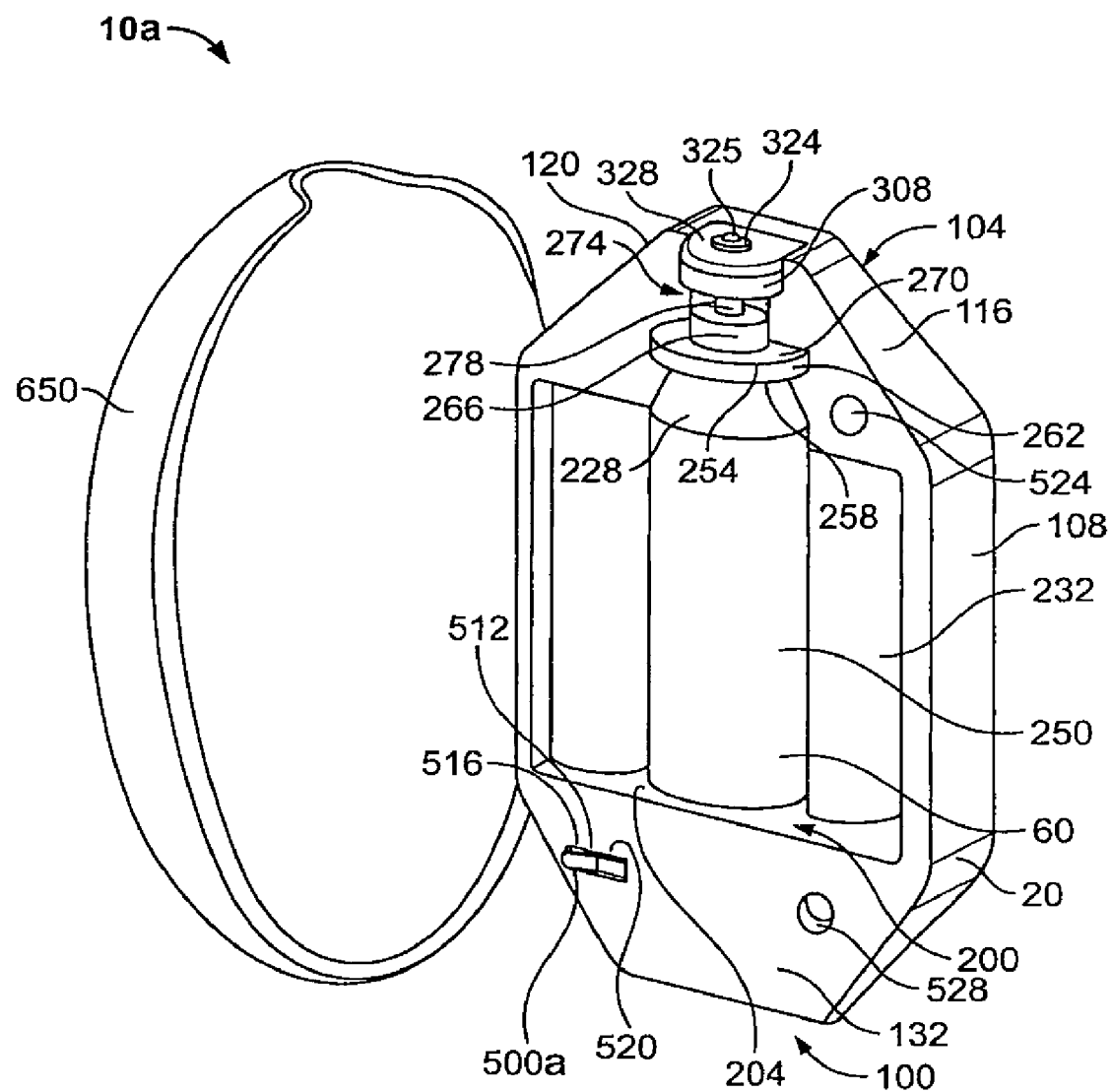
FIG. 13 is an isometric view of another dispenser having an open front cover.
Figure 14:
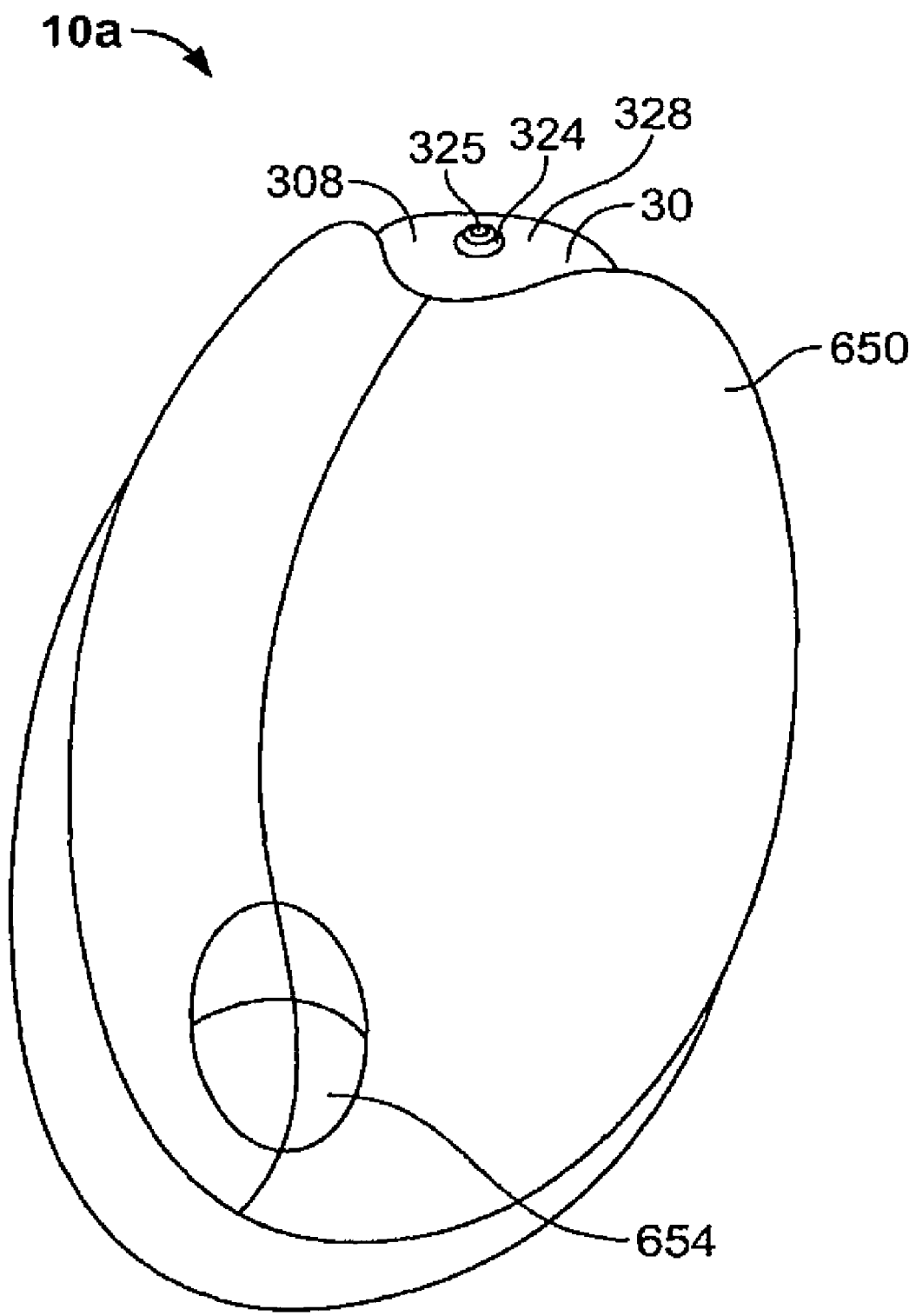
FIG. 14 is an isometric view of the dispenser of FIG. 13 with the front cover closed.

FIGS. 13-16 depict several other embodiments of the present dispensers 10, 10a, and 10b, which are characterized by the inclusion of a front cover 650 disposed adjacent the front side 132 of the housing 20. FIG. 13 shows one specific embodiment of a front cover 650 in an open position. FIG. 14 depicts the embodiment of FIG. 13 in a closed position. Closing the front cover 650 prevents the user from viewing the batteries 232 and the container 60. The front cover 650 is mounted to the first or second sidewall by a hinge (not shown). The front cover 650 is also contoured adjacent the overhang member 308 to ensure that the front cover 650 does not block or obstruct the flow path of the fluid dispensed from the second orifice 324 of the actuator arm 30.

The front cover 650 of FIGS. 13 and 14 is fashioned to allow the second switch 528 to be depressed when the front cover 650 is closed. The user applies pressure to the front cover 650 adjacent an area 654 to actuate the second switch 528. When the user presses the area 654, the front cover 650 is forcibly rotated about the hinge from the closed position a sufficient distance to cause an inside of the front cover 650 to contact and depress the second switch 528. Release of the front cover 650 after actuation of the second switch 528 causes the front cover 650 to flex back into the closed position. In other embodiments, the front cover could be depressible in one or more areas to actuate one or more switches. Still further, some embodiments have buttons or other switches disposed within the front cover 650.

Figure 15:
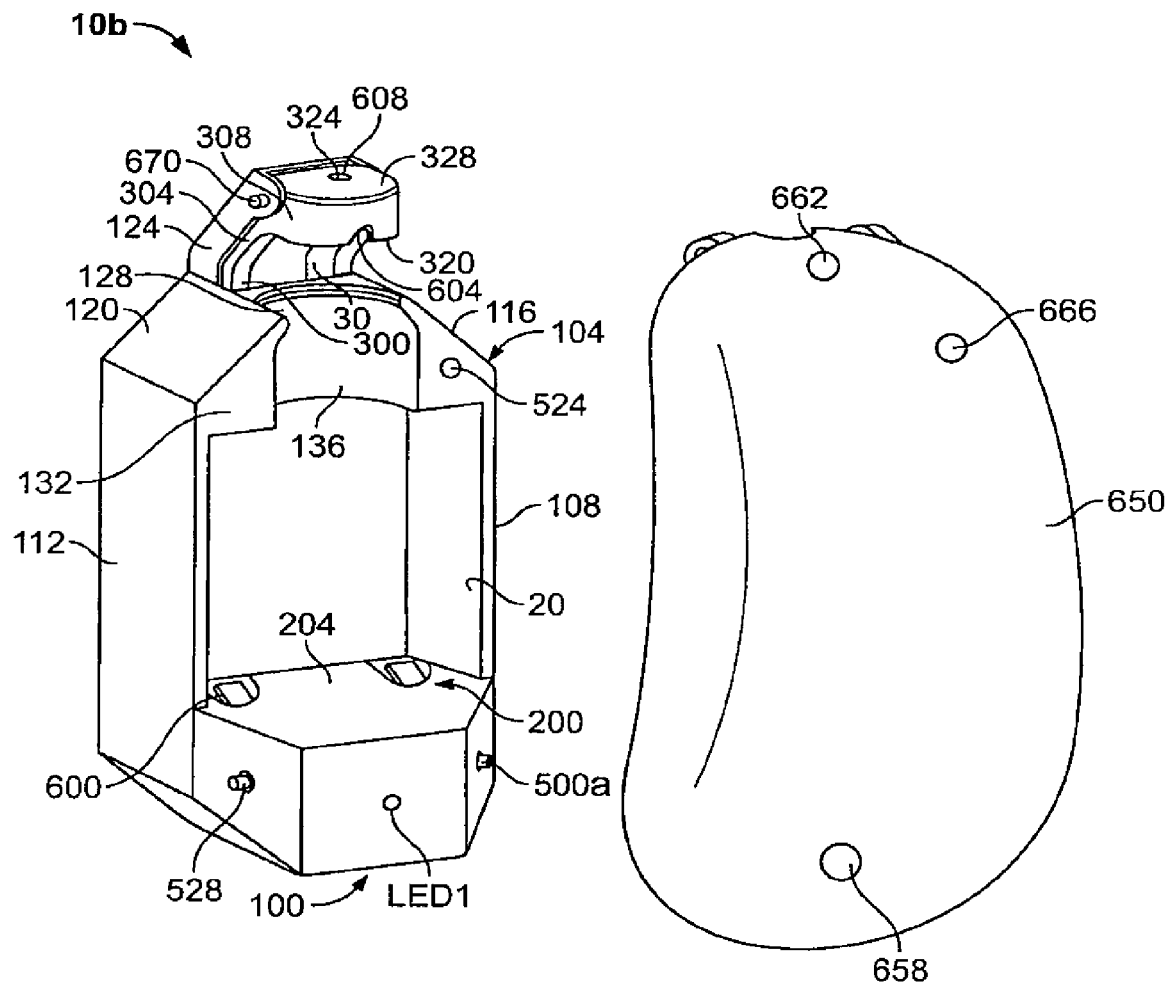
FIGS. 15 and 16 are exploded isometric views of further dispensers with alternate front covers.

In another embodiment shown in FIG. 15, the front cover 650 includes an LED port 658 to view LED1 therethrough. The present embodiment also includes a spray slot 662 to allow fluid dispensed from the dispensing bore 324 to pass therethrough. A sensor port 666 is also provided to allow a sensory access path for the sensor 524. The front cover 650 is opened by pivoting same upwardly around a hinge 670. Further, the front cover 650 of FIG. 15 is also depressible adjacent the base portion 100 of the housing 20, wherein depression of the front cover 650 results in actuation of the second switch 528.

Figure 16:
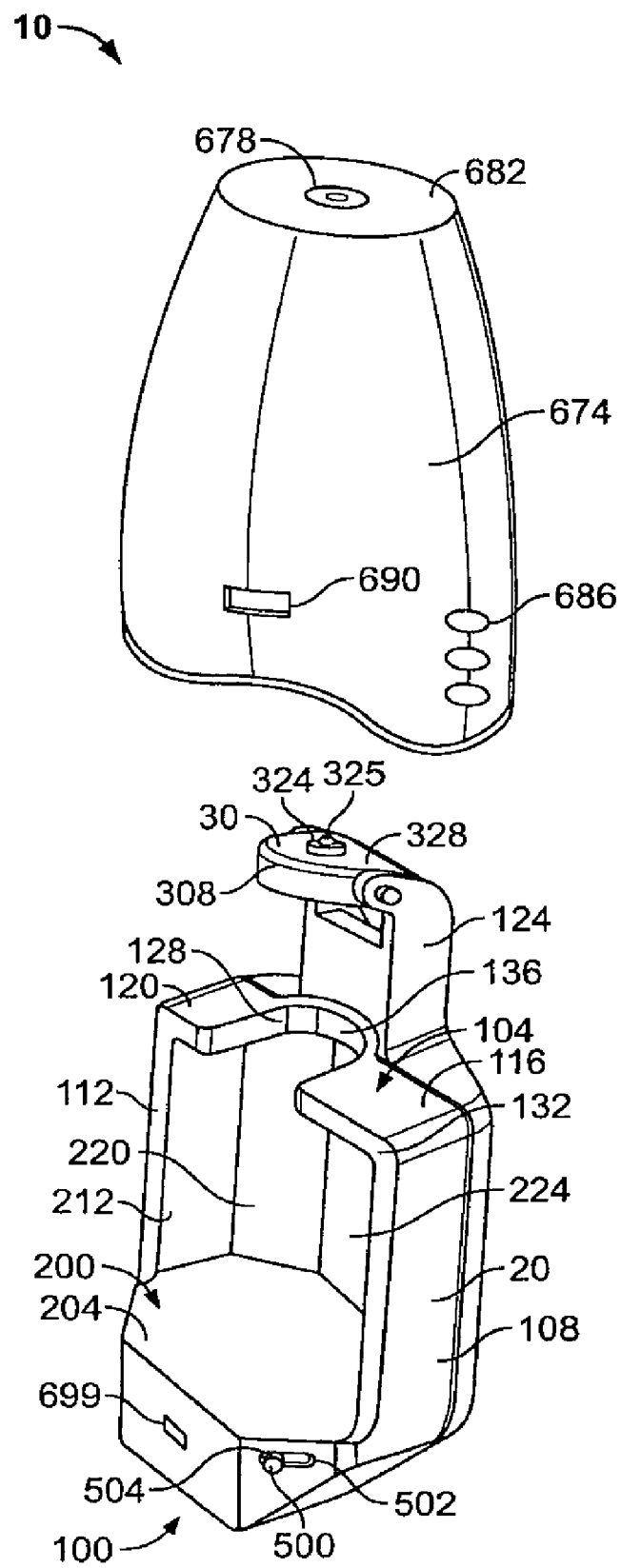

FIG. 16 depicts another dispenser 10 having a wraparound cover 674. The wraparound cover 674 fittingly engages with the housing 20 to cover the front side 132, the outer rear panel 148, and the sidewalls 108, 112. The wraparound cover 674 includes a hole 678 within a top end 682 thereof that is in alignment with the dispensing bore 324. The hole 678 allows fluid sprayed from the dispensing bore 324 to pass therethrough and reach the atmosphere. Preferably, the wraparound cover 674 includes a release mechanism 686 that disengages the wraparound cover 674 from the housing 20. In the present embodiment, the user depresses areas of the wraparound cover 674 adjacent the sidewalls 108, 112 to disengage an inside undercut 690 of the wraparound cover 674 from an undercut 694 on the front side 132 of the base portion 100. Disengaging the undercuts 690, 694 from each other allows the wraparound cover 674 to be removed from the housing 20.

An alternative embodiment of a dispenser 10c is depicted in FIGS. 17-22, which is similar to the embodiment depicted in FIG. 12 in that it generally comprises an octagonal housing 20 with the actuator arm 30 being similarly disposed for depression of the valve stem 278 of the container 60. However, the present embodiment may be altered to fully or partially encompass any of the differing structural and functional aspects described herein.

Figure 17:
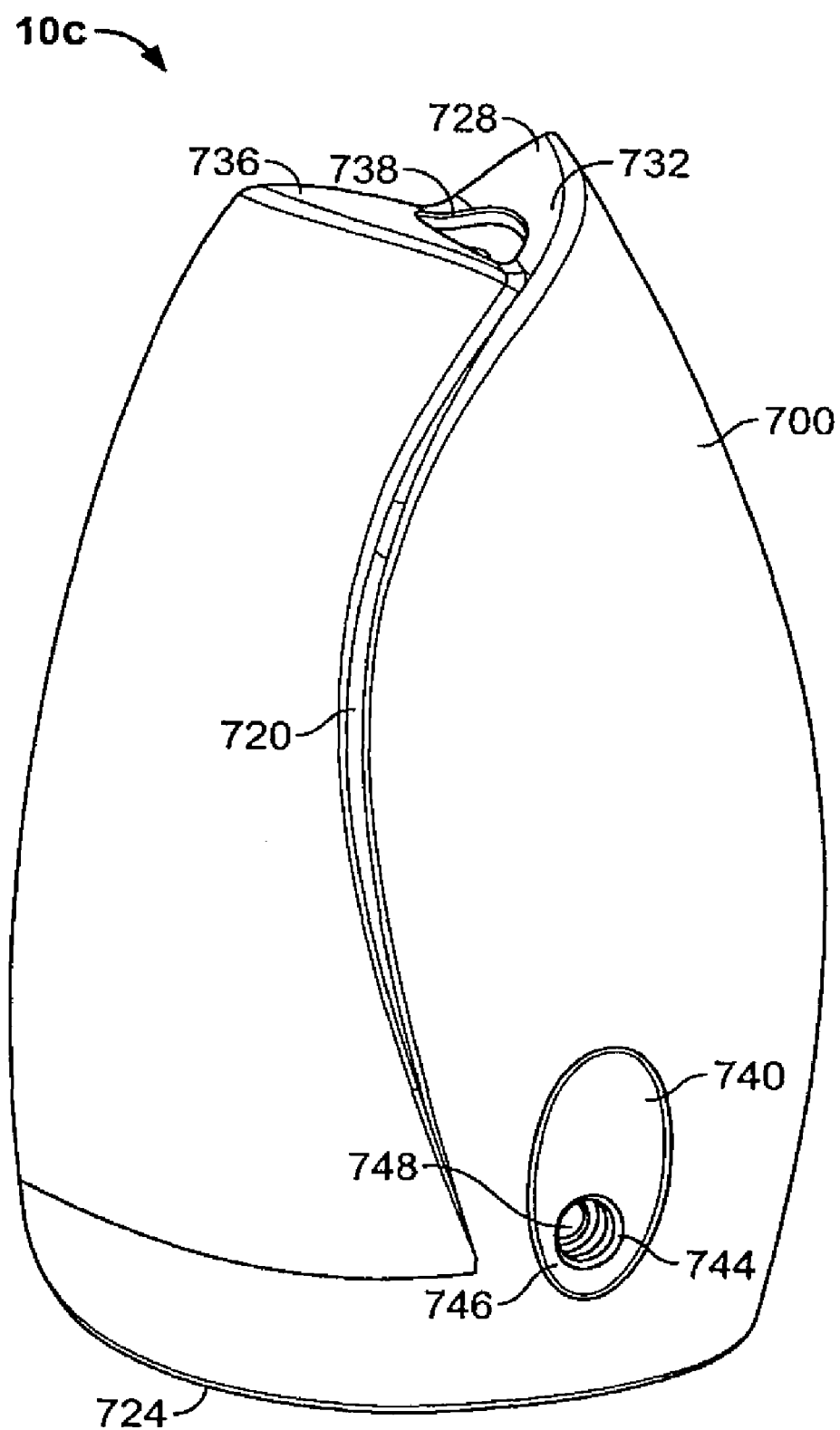
FIG. 17 is an isometric view of a different dispenser.
Figure 18:
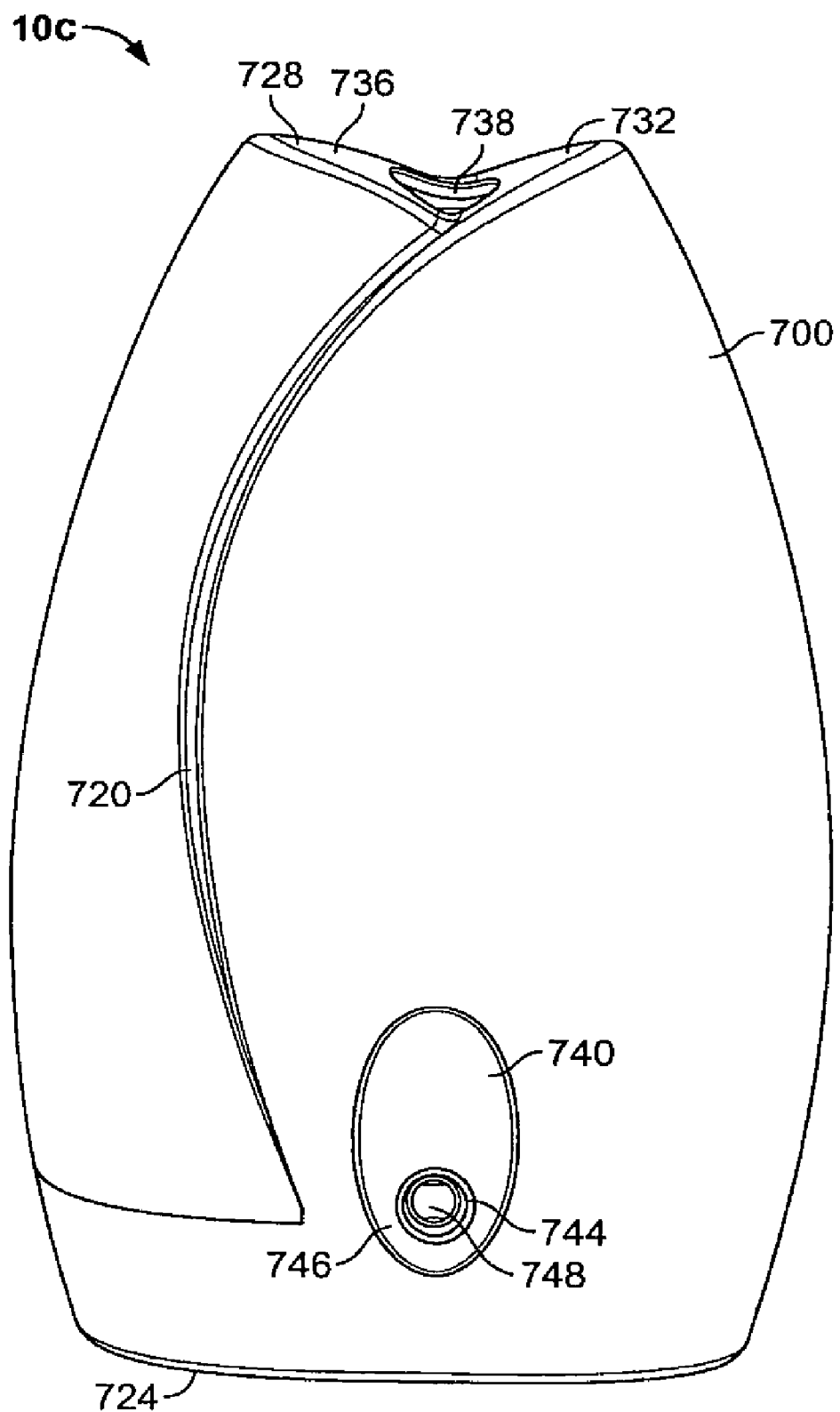
FIG. 18 is a front elevational view of the dispenser of FIG. 17.
Figure 19:
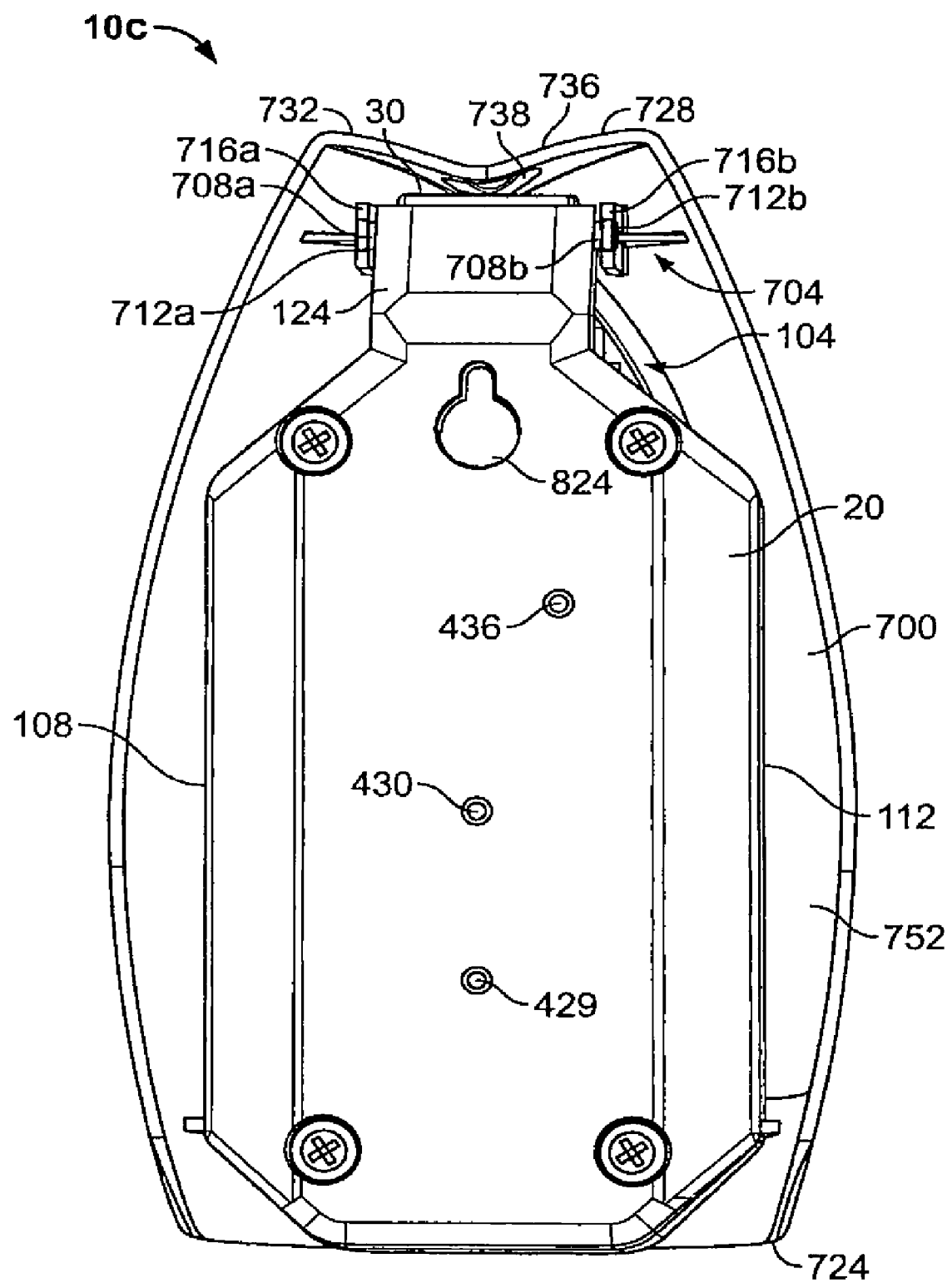
FIG. 19 is a rear elevational view of the dispenser of FIG. 17.

FIGS. 17-19 depict a tulip-shaped dispenser cover 700 secured to the housing 20. The cover 700 wraps around the side walls 108, 112, the top portion 104, the actuator arm 30, and the front side 132 of the housing 20 in a closed condition, thereby leaving a bottom end of the base portion 100 and the rear side of the housing 20 exposed. The cover 700 is pivotally attached to the actuator arm cover 124. The cover 700 is moved into an open position by rotating same about a hinge 704 comprising two cylindrical members 708a, 708b extending outwardly from the actuator arm cover 124. The cover 700 includes corresponding grooves 712a, 712b disposed on inwardly extending bars 716a, 716b that pivotally mate with the two cylindrical members 708a, 708b, respectively.

A curvilinear groove 720 extends from a lower end 724 of the cover 700 to an upper end 728 thereof and partially defines a first portion 732 of the upper end 728. A second portion 736 is disposed adjacent the first portion 732 and, in conjunction with the first portion 732, causes the upper end 728 to have a general V-shape. A circular hole 738 extends through a center of the V-shaped upper end 728. The circular hole 738 is aligned with the dispensing bore 324 of the actuator arm 30 in the closed position. The circular hole 738 is sized to allow uninterrupted or partially interrupted passage of fluid from the dispensing bore 324 therethrough. Further, an oval shaped recess 740 is disposed in the lower end 724 of the cover 700. A second circular hole 744 extends through the cover 700 at a bottom portion 746 of the oval recess 740. The second circular hole 744 is aligned with a sensor 748 within the bottom portion 100 of the housing 20 when the cover 700 is in a closed position. Still further, an inside surface 752 of the cover 700 includes an activation bar (not shown) for engagement with a push button switch 756 disposed on the bottom portion 100 of the housing 20. Pressing the cover 700 adjacent the push button switch 756 causes same to be depressed and for the electrical components of the dispenser 10c to be manually activated.

Figure 20:
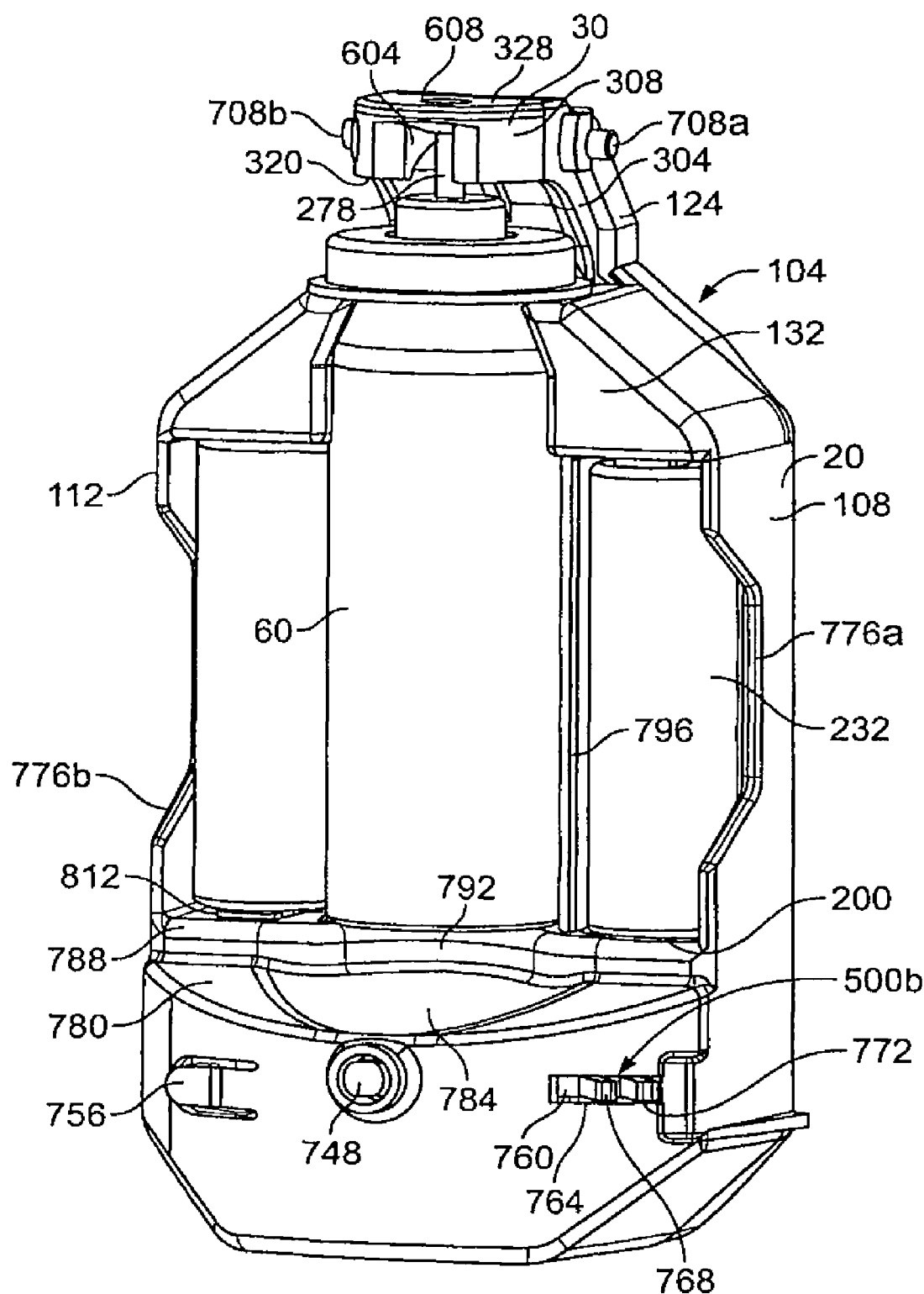
FIG. 20 is view similar to that of FIG. 17, except that a dispensing cover has been removed to show a front side of the dispenser.
Figure 21:
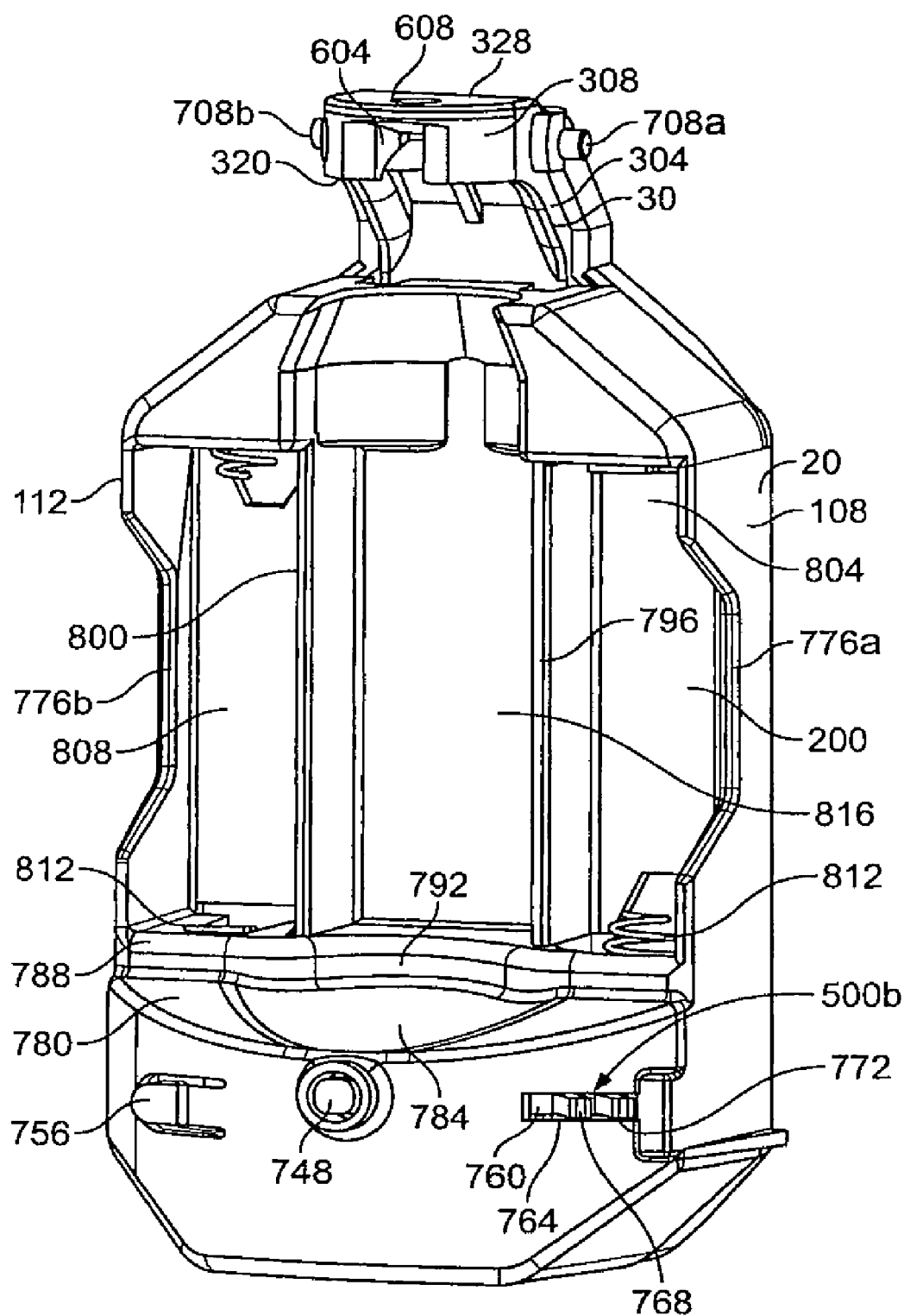
FIG. 21 is a view similar to that of FIG. 20, except that a fluid container and batteries have been removed from the front side of the dispenser.

FIGS. 20 and 21 depict the dispenser 10c without the cover 700. The housing 20 of the dispenser 10c is similar to that of dispenser 10b except that the dispenser 10c includes numerous curved surfaces and shaped edges in contrast to the sharp lines of dispenser 10b depicted in FIG. 12. One skilled in the art will find the aesthetic differences between dispensers 10c and 10b to be apparent from the provided FIGS. 12 and 17-21. However, several differences between the dispensers 10b and 10c are provided below to provide a more complete description of the dispenser 10c.

The base portion 100 of the dispenser 10c adjacent the front side 132 comprises a curved surface having a switch 500b disposed therein. The switch 500b is disposed adjacent the first side wall 108, whereas the push button switch 756 is disposed adjacent the second side wall 112 and the sensor 748 is disposed in a center of the base portion 100. The switch 500b is adapted to be toggled between four positions. A first position 760 deactivates the dispenser 10c. Movement of the switch 500b to any one of a second position 764, third position 768, or fourth position 772 energizes the electrical components of the dispenser 10c and causes the dispenser 10c to operate in a combined timed and sensing mode of operation responsive to the output of the sensor 748. While the sensor 748 is preferably a photocell light sensor capable of detecting changes in light, the sensor 748 may comprise any type of sensor known to those skilled in the art and/or as discussed herein.

Activation of the dispenser 10c may be initiated by manual input, sensory input, and/or the lapsing of a time interval as discussed in the embodiments above. It is preferred, however, that the second position 764 provide for about a twenty minute timed interval between automatic spray periods, the third position 768 provide for about a forty minute timed interval between automatic spray periods, and the fourth position 772 provide for about an eighty minute timed interval between automatic spray periods. In another preferred embodiment, the second position 764 provides an about ten minute timed interval, the third position 768 provides an about twenty minute timed interval, and the fourth position 772 provides an about forty minute timed interval. However, as noted above with respect to the prior embodiments, the time intervals may comprise any period of time desired including, for example, a time interval between about ten minutes to about eighty minutes or more, or about 10 minutes or less. It is also envisioned that different time intervals will be provided on the basis of the fluid to be dispensed and/or varying user preferences and/or inputs.

Figure 22:
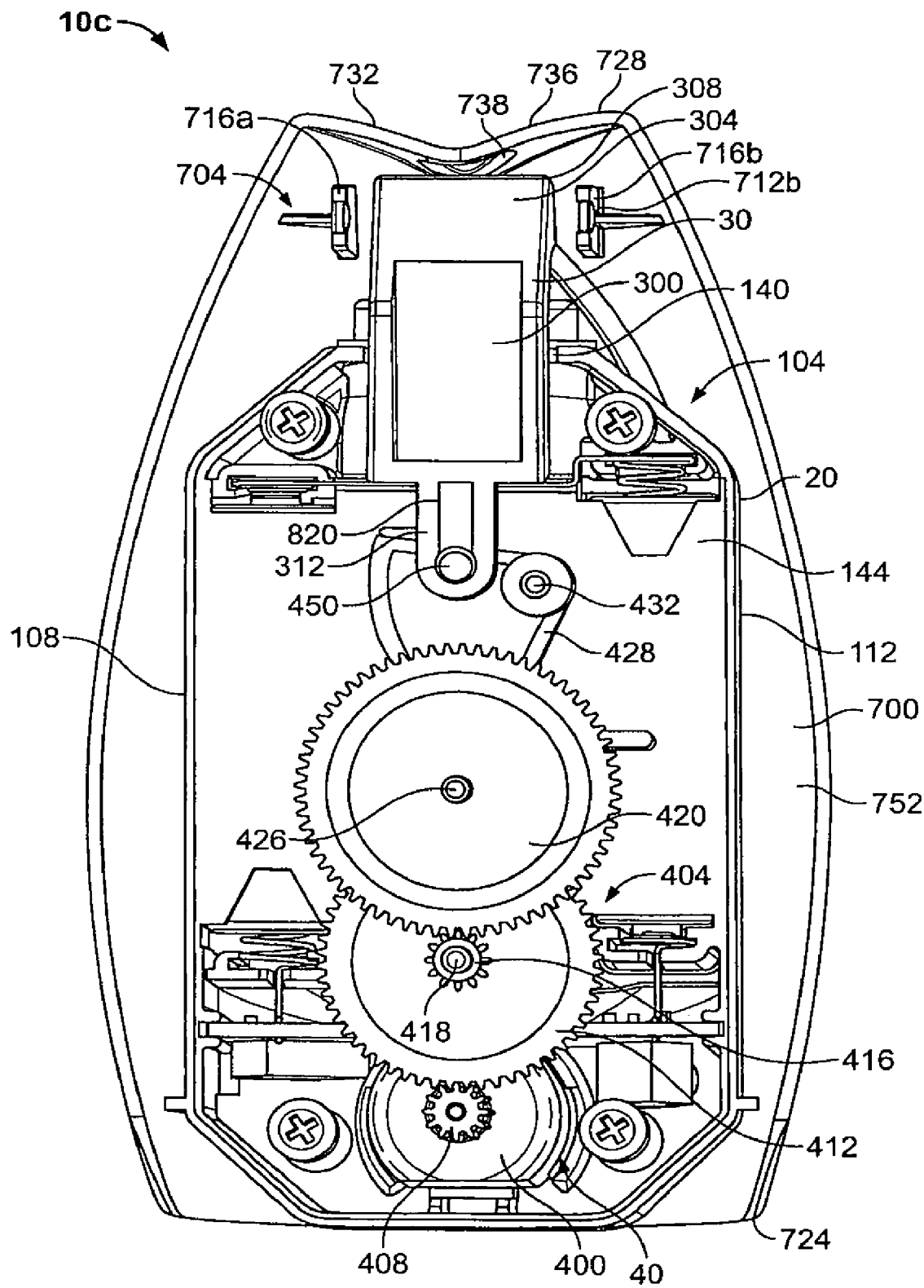
FIG. 22 is a view similar to that of FIG. 19, except that a rear panel has been removed to show a drive unit and an actuator arm.
Figure 23:
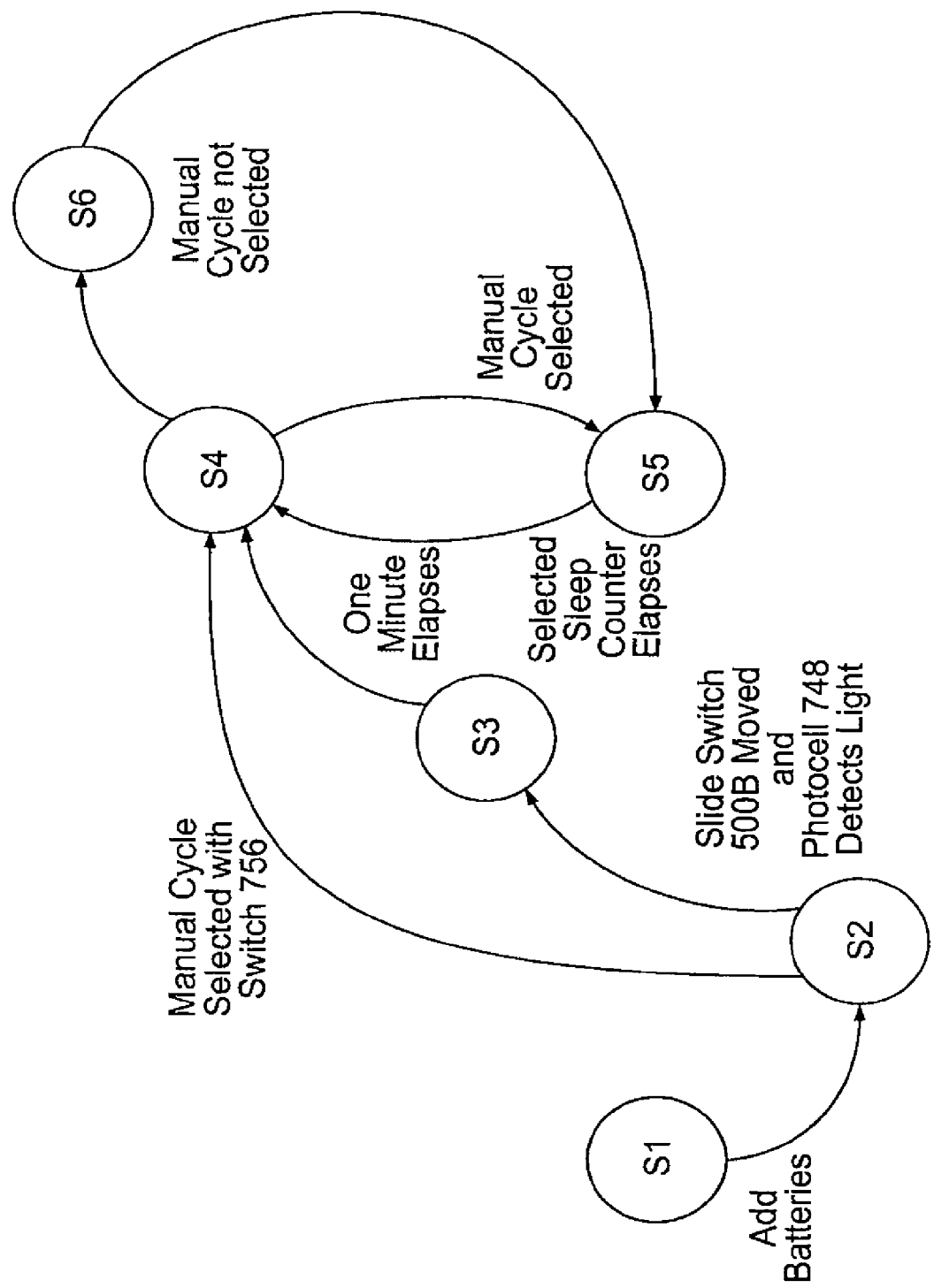
FIG. 23 is a state diagram depicting the operation of the dispenser of FIGS. 17-22 according to a third operational sequence.

Operation of the embodiment of FIGS. 17-22 is illustrated by the state diagram of FIG. 23. A state S1 comprises a condition wherein the dispenser 10c is off and the batteries 232 have not been inserted therein. Once the batteries 232 have been properly inserted into the dispenser 20c, the dispenser 10c assumes a state S2 wherein the unit awaits actuation of either of the switches 500b or 756. If a user moves the slide switch 500b to one of the twenty, forty, or eighty minute positions and the photocell sensor 748 detects light, the dispenser 10c transitions to a state S3 at which a predetermined delay period is timed. In the preferred embodiment, the delay period comprises about one minute. Also while in the state S3, the dispenser 10c initializes three sleep counters that count twenty, forty, and eighty minute sleep periods.

Upon expiration of the predetermined time period (e.g., one minute), the dispenser 10c transitions to a state S4 whereupon the drive motor 400 is energized for about one-half second. As previously noted, this motor 400 energization operates through the gear train 404 to depress the valve stem 278 and causes emission of ingredients stirred within the container 60. The dispenser 10c can also transition from the state S2 directly to the state S4 if the user depresses the manual push button switch 756.

Upon expiration of the one-half second spray period (which, in other embodiments, may have a duration other than one-half second) the dispenser 10c transitions to a state S5 if the manual cycle was previously selected. While in the state S5, the dispenser 10c either starts the sleep counters (if the sleep counters have not already been started) or continues the sleep counters if the sleep counters were previously actuated. The dispenser 10c remains in the state S5 until the sleep counter selected by the user via the slide switch 500b has elapsed, whereupon the dispenser 10c transitions or returns to the state S4 to cause spraying of the contents of the container 60. It should be noted that the transition from the state S5 to the state S4 under these circumstances results also in a resetting of the sleep counters just prior to transitioning of the dispenser 10c to the state S4.

The dispenser 10c transitions from the state S4 to a state S6 upon the end of a spraying period provided that the transitioning into the state S4 did not occur as a result of selection of a manual cycle. While in the state S6, the sleep counters are reset and the dispenser 10c automatically transitions to the state S5.

It should be noted that the dispenser 10c can transition from any of the states S3-S6 to the state S2 if the slide switches 500b move to the off position. Further, the dispenser 10c transitions from any of the states S2-S6 to the state S1 if either or both of the batteries 232 are removed.

The operation depicted in FIG. 23 may be carried out in a similar matter as described above and as known to one skilled in the art. Conventional discrete electronic components, a microprocessor, a microcontroller, and an application specific integrated circuit are contemplated as being useful in carrying out the present operation.

For purposes of further explaining how the dispenser 10c operates, the following example is illustrative of a typical embodiment. The dispenser 10c is placed in a room that is provided with no illumination. The switch 500b is initially in the first position 760 so that the dispenser 10c is inactive. The switch is thereafter toggled to the second position 764 that is utilized to initiate an automatic spray time interval of about twenty minutes. Simultaneously, the toggling of the switch 500b to the second position 764 activates the sensor 748. The sensor 748 comprises a light sensor similar to those described above. The sensor 748 fails to register a sufficient amount of ambient light and prevents controller 532 from activating the dispenser 10c. A person thereafter enters the room and turns on a light. A sufficient amount of ambient light is generated from the light to register with the sensor 748. Upon completion of a startup delay period, the drive unit 40 is directed to discharge fluid from the dispenser 10c during a first spraying period. The startup delay period is preferably about one minute long. Upon completion of the first spraying period, the dispenser 10c enters a first sleep period that lasts the predetermined time interval of about twenty minutes. Upon expiration of the first sleep period the drive unit 40 is actuated to discharge fluid during a second spraying period. Automatic operation thereafter continues with alternating sleep and spraying periods. At any time during a sleep period, the user can manually activate the dispenser 10c for a selectable or fixed period of time by depressing the push button switch 756. Manual activation of the dispenser 10c does not effect the current sleep period or when the next spraying period commences. The user enters the room again after several sleep and spraying periods have elapsed and turns off the light. The sensor 748 no longer registers a sufficient amount of ambient light and deactivates the dispenser 10c.

Further, while the combined timed and sensing mode of operation may operate in a similar manner as described above, in a different embodiment the operation is responsive to a different set of consumer desires. Specifically, activation of the dispenser 10c in response to sensory input may cause a person or animal to become frightened or surprised upon hearing the noise of the dispenser 10c while spraying or by the unexpected nature of the spraying. This may occur if the dispenser 10c automatically sprays when a person or animal moves past the dispenser 10c or at a time thereafter while they are still in the vicinity of the dispenser 10c. Further, some people and animals may not like to be exposed to a strong initial burst of fluid that may accompany a spraying from the dispenser 10c. Therefore, the combined timed and sensing mode of operation preferably prevents the automatic spraying of the dispenser 10c when a person or animal moves past or is in the vicinity of the dispenser 10c.

In a first example, the switch 500b is toggled to the second position 764, thereby providing an about twenty minute timed interval between automatic spray periods. However, other time intervals such as about fifteen minutes or more may be used. After a first sleep period of about twenty minutes the dispenser 10c automatically discharges fluid during a first spraying period. Upon completion of the first spraying period the dispenser 10c enters a second sleep period for the same twenty minute duration. This alternating pattern of spraying periods and sleep periods continues until the dispenser 10c is turned off or the sensor 748 is activated. During the second sleep period a person enters the room the dispenser 10c is disposed within and crosses a sensory path of the sensor 748. However, the person leaves prior to expiration of the second sleep period. Regardless of whether the sensor 748 is active or asleep, the controller 532 does not alter the timing of the activation of the second spray period if it receives a signal from the sensor 748 during the sleep period. A second person also enters the room prior to the expiration of the second sleep period and remains in the room until the end thereof. The sensor 748 registers movement across a sensory path at the end of the second sleep period and transmits a signal to the controller 532 to prevent activation of the second spraying period. The controller 532 thereafter enters into another sleep period for a delay time interval such as about two minutes. However, other delay time intervals such as about five minutes or less may be used. After the two minute delay time interval ends the sensor 748 repeats the step of determining whether any motion registers across the sensory path. If motion is registered by the sensor 748, a second delay time interval of the same duration is initiated. This step is repeated until no motion is registered at the end of any delay time interval. However, in the present example the sensor 748 does not register any motion and sends a signal to the controller 532 to activate the dispenser 10c and spray. A third sleep mode is entered into for a duration of about twenty minutes. Thereafter, the prior steps are carried out in a similar manner.

In a second example, the same scenario as discussed above produces identical results up until the sensor 748 registers movement from the second person after the second sleep period has ended. In this example, the sensor 748 sends a signal to the controller 532 to prevent activation of the second spray period and thereafter continually attempts to register movement across the sensory path to determine if there is movement in the room. In the present example, the second person moves within the sensory path for approximately thirty seconds and thereafter stands still for another thirty seconds before initiating movement across the sensory path again to leave the room. During the thirty second time period the person is moving the sensor 748 registers movement and prevents activation of the second spray period. Thereafter, the sensor 748 does not register movement and sends a signal to the controller 532 to reset the timer for a delay time interval of about two minutes. However, the sensor 748 still attempts to continually register movement across the sensory path during the delay time interval. In the present example, the sensor 748 registers movement after the thirty second interval of no movement. In response, the sensor 748 continually attempts to register movement until none is detected, wherein the sensor 748 then sends a signal to restart the delay time interval. After the two minute delay time interval the dispenser 10c is activated. A third sleep period is thereafter entered into for a duration of about twenty minutes. The prior steps are carried out in a similar manner until the dispenser 10c is deactivated.

In any of the examples provided above, an initial startup delay period may be provided prior to a first spraying period after the dispenser 10c is activated. Further, manual activation of the dispenser 10c by way of the push button switch 756 may be carried out in a similar manner as described in the other embodiments herein. Still further, any variation in timing or operation of any aspect of the dispensers 10, 10a, 10b is applicable to the present embodiments.

FIGS. 20 and 21 also show that the side walls 108, 112 extend between the bottom portion 100 and the top portion 104. The side walls 108, 112 include cut out portions 776a, 776b to assist in insertion and removal of the batteries 232 from the dispenser 10c. The batteries 232 are inserted through the front side 132 of the housing 20 and into the recess 200. The recess 200 comprises a relatively flat bottom side 780 having a curved recess 784 disposed within a center thereof. A stepped portion 788 extends upwardly from the bottom side 780 between the side walls 108, 112. A grooved portion 792 having a width coextensive with a width of the curved recess 784 is provided within the stepped portion 788. A first inner wall 796 and a second inner wall 800 are disposed between and parallel to the side walls 108, 112. The first inner wall 796 and the side wall 108 define a first compartment 804 and the second inner wall 800 and the side wall 112 define a second compartment 808. The first and second compartments 804, 808 are sized to retain the batteries 232 therein and are provided with battery terminals 812 in electrical communication with the circuitry of the dispenser 10c. A retention tab (not shown) depends from the top portion 104 within both of the first and second compartments 804, 808 to assist in preventing the batteries 232 from dislodging or accidentally being removed from the dispenser 10c.

A third compartment 816 is provided between the first and second compartments 804, 808 for receipt of the container 60. A bottom end of the container rests on the stepped portion 788 adjacent the grooved portion 792. A finger of a user may be inserted within the grooved portion 792 to assist in the removal or insertion of the container 60. The inner walls 796, 800 are adapted to provide a relatively close fit with the container body 250. A top portion of the container 60 extends through the slot 128 disposed between the first and second shoulders 116, 120 of the top portion 104. The slot 128 is contoured to closely fit the top portion and the angled neck 228 of the container 60. The mounting cup 254 is disposed against the top portion 104 between the shoulders 116, 120.

FIGS. 20-22 show that the positioning and shape of the actuator arm 30 and the actuator arm cover 124 with respect to each other and the other functional elements of the dispenser 10c are similar to those shown in FIG. 12. Several differences of particular note are the provision of substantially smoother and curved surfaces and a rectangular groove within portions of the main and intermediate portions 300, 304 of the actuator arm 30. Another difference is the contouring of the second recess 608 into an oval shaped recess having a cross-sectional area that narrows non-uniformly from the upper side 328 of the overhang portion 308 toward the dispensing bore 324 in an interior thereof. Further, the dispensing bore 324 is offset from a center of the second recess 608.

The drive motor 400 and the associated gear train 404 used to depress the valve stem 278 operate in substantially the same way as described above. One particular difference is the positioning and orientation of the third pinion 424 and the lever gear 428. Specifically, the third pinion 424 is disposed adjacent the inner rear panel 144 as opposed to the outer rear panel 148. Similarly, the lever gear 428 is on a side of the idler gear 420 that is now closer to the inner rear panel 144. Further, the axle 432 that extends from the inner rear panel 144 to the hole 436 of the outer rear panel 148 is now closer to the side wall 112 than the side wall 108. The molded rib 454 projecting from the inner rear panel 144 is also disposed closer to the side wall 112. In contrast to the previously described embodiments, the lever gear 428 is rotated counter-clockwise to pull the actuator arm 30 downwardly into the discharge position. Still further, the offset pin 450 is disposed in a truncated racetrack shaped groove 820 as opposed to a circular hole.

The dispenser 10c is preferably disposed on a support surface while in an active state. In one embodiment, the bottom end of the bottom portion 100 is adapted to be placed on a relatively flat support surface. Further, the dispenser 10c may be rotated to rest the outer rear panel 148 adjacent the support surface. In a different embodiment, an adhesive is applied to the outer rear panel 148 to adhere the dispenser 10c to a substantially vertical support surface. In yet another embodiment, a hole 824 is provided in the outer rear panel 148 for attaching the dispenser 10c to a corresponding hook or member extending from a substantially vertical support surface.

INDUSTRIAL APPLICABILITY

The dispenser described herein advantageously allows for the contents of an aerosol container to be sprayed into the atmosphere. The dispenser utilizes a compact and lightweight design to afford it a broad spectrum of potential applications throughout numerous areas of a house or a workplace.

Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. The exclusive rights to all modifications which come within the scope of this disclosure are reserved.

We claim:

1. A method of operating a dispensing unit, comprising:
   providing a power source to a dispensing unit that includes a housing having an aerosol container disposed therein and an actuator arm;
   activating the dispensing unit in response to a minimum threshold of light being sensed by a light sensor;

selecting a sleep period interval between spray operations;

moving the actuator arm after completion of a startup delay period from a pre-actuation position to a discharge position along a path substantially parallel to an axial length of the container to actuate a nozzle of the container to discharge a fluid from the container; and alternating automatically between the sleep period having a duration commensurate with the selected sleep period interval and a discharge period during which the fluid is dispensed from the container.

2. The method according to claim 1 further including the step of manually activating the dispensing unit for the duration of the discharge period during the sleep period interval.

3. The method according to claim 2, wherein when the dispensing unit is manually activated the sleep period interval is not reset, and the fluid is discharged during the automatic discharge period at the end of the sleep period interval.

4. The method according to claim 2, wherein the dispensing unit is manually activated by depressing a switch disposed on the housing.

5. The method according to claim 1, wherein the duration period comprises about a half of one second.

6. The method according to claim 1, wherein the startup delay period ranges from about one minute to about three minutes.

7. The method according to claim 6, wherein the startup delay period is about one minute.

\* \* \* \* \*